United States Patent
Nishide et al.

(10) Patent No.: US 9,818,957 B2
(45) Date of Patent: Nov. 14, 2017

(54) ORGANIC LIGHT EMITTING ELEMENT

(71) Applicant: CANON KABUSHIKI KAISHA, Tokyo (JP)

(72) Inventors: Yosuke Nishide, Kawasaki (JP); Jun Kamatani, Tokyo (JP); Hiroki Ohrui, Kawasaki (JP); Yojiro Matsuda, Kawasaki (JP); Masanori Muratsubaki, Tokyo (JP); Satoru Shiobara, Funabashi (JP); Tetsuo Takahashi, Kawaski (JP); Haruna Iida, Nagoya (JP)

(73) Assignee: Canon Kabushiki Kaisha, Tokyo (JP)

( * ) Notice: Subject to any disclaimer, the term of this patent is extended or adjusted under 35 U.S.C. 154(b) by 194 days.

(21) Appl. No.: 14/784,333

(22) PCT Filed: Feb. 2, 2015

(86) PCT No.: PCT/JP2015/000444
§ 371 (c)(1),
(2) Date: Oct. 14, 2015

(87) PCT Pub. No.: WO2015/115116
PCT Pub. Date: Aug. 6, 2015

(65) Prior Publication Data
US 2016/0079544 A1    Mar. 17, 2016

(30) Foreign Application Priority Data

Feb. 3, 2014 (JP) .................................. 2014-018560
Jan. 7, 2015 (JP) .................................. 2015-001211

(51) Int. Cl.
*H01L 29/08* (2006.01)
*H01L 51/50* (2006.01)
(Continued)

(52) U.S. Cl.
CPC ........ *H01L 51/0067* (2013.01); *C07D 209/86* (2013.01); *C07D 213/22* (2013.01);
(Continued)

(58) Field of Classification Search
CPC .. C07D 209/86; C07D 213/22; C07D 213/26; C07D 213/30; C07D 213/38;
(Continued)

(56) References Cited

U.S. PATENT DOCUMENTS 8,093,587 B2    1/2012   Shiratori et al.
2005/0011005 A1    1/2005   Borda
(Continued)

FOREIGN PATENT DOCUMENTS

JP    2001-188261 A    7/2001
JP    2008-214307 A    9/2008
(Continued)

OTHER PUBLICATIONS

B. Broker et al., "Gold Work Function Reduction by 515 hY with an Air-Stable Molecular Donor Layer", Appl. Phys. Lett. 93, 243303 (2008).

Primary Examiner — Dawn Garrett
(74) Attorney, Agent, or Firm — Fitzpatrick, Cella, Harper & Scinto

(57) ABSTRACT

Provided is an organic light emitting element having stable performance in the air. The organic light emitting element includes: an anode; a cathode; and a first organic compound layer placed between the anode and the cathode, in which: the organic light emitting element further includes a first organic compound layer placed between the cathode and the emission layer, and a second organic compound layer placed between the emission layer and the first organic compound layer, and brought into contact with the first organic com-
(Continued)

pound layer; the first organic compound layer contains a first organic compound; the second organic compound layer contains a second organic compound; and the first organic compound includes an organic compound represented by the following general formula [1], and the second organic compound includes an organic compound different from the first organic compound

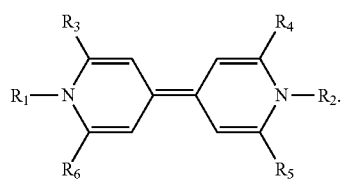

[1]

16 Claims, 3 Drawing Sheets

(51) Int. Cl.
| | |
|---|---|
| H01L 51/00 | (2006.01) |
| C07D 221/04 | (2006.01) |
| C07D 409/14 | (2006.01) |
| C07D 249/08 | (2006.01) |
| C07D 251/24 | (2006.01) |
| C07D 471/04 | (2006.01) |
| C07D 213/22 | (2006.01) |
| C07D 213/26 | (2006.01) |
| C07D 213/30 | (2006.01) |
| C09K 11/06 | (2006.01) |
| C07D 405/14 | (2006.01) |
| C07D 413/14 | (2006.01) |
| C07D 311/86 | (2006.01) |
| C07D 333/76 | (2006.01) |
| C07D 335/16 | (2006.01) |
| C07D 235/18 | (2006.01) |
| C07D 403/14 | (2006.01) |
| C07D 471/06 | (2006.01) |
| C07D 493/06 | (2006.01) |
| C07D 271/107 | (2006.01) |
| C07D 209/86 | (2006.01) |
| C07D 213/38 | (2006.01) |
| C07D 213/61 | (2006.01) |
| C07D 213/64 | (2006.01) |
| H05B 33/08 | (2006.01) |
| H01L 27/32 | (2006.01) |
| H01L 29/24 | (2006.01) |
| H01L 29/786 | (2006.01) |

(52) U.S. Cl.
CPC ......... *C07D 213/26* (2013.01); *C07D 213/30* (2013.01); *C07D 213/38* (2013.01); *C07D 213/61* (2013.01); *C07D 213/64* (2013.01); *C07D 221/04* (2013.01); *C07D 235/18* (2013.01); *C07D 249/08* (2013.01); *C07D 251/24* (2013.01); *C07D 271/107* (2013.01); *C07D 311/86* (2013.01); *C07D 333/76* (2013.01); *C07D 335/16* (2013.01); *C07D 403/14* (2013.01); *C07D 405/14* (2013.01); *C07D 409/14* (2013.01); *C07D 413/14* (2013.01); *C07D 471/04* (2013.01); *C07D 471/06* (2013.01); *C07D 493/06* (2013.01); *C09K 11/06* (2013.01); *H01L 27/3244* (2013.01); *H01L 29/24* (2013.01); *H01L 29/7869* (2013.01); *H01L 51/005* (2013.01); *H01L 51/0052* (2013.01); *H01L 51/0053* (2013.01); *H01L 51/0055* (2013.01); *H01L 51/0056* (2013.01); *H01L 51/0058* (2013.01); *H01L 51/0072* (2013.01); *H05B 33/0896* (2013.01); *C09K 2211/1029* (2013.01); *H01L 51/0006* (2013.01); *H01L 51/5012* (2013.01); *H01L 51/5076* (2013.01); *H01L 51/5092* (2013.01); *H01L 2251/308* (2013.01); *H01L 2251/5361* (2013.01); *H01L 2251/556* (2013.01)

(58) Field of Classification Search
CPC .. C07D 213/61; C07D 213/64; C07D 221/04; C07D 235/18; C07D 249/08; C07D 251/24; C07D 271/107; C07D 311/86; C07D 333/76; C07D 335/16; C07D 403/14; C07D 405/14; C07D 409/14; C07D 413/14; C07D 471/04; C07D 471/06; C07D 493/06; C09K 11/06; C09K 2211/1029; H01L 2251/308; H01L 2251/5361; H01L 2251/556; H01L 27/3244; H01L 29/24; H01L 29/7869; H01L 51/0006; H01L 51/005; H01L 51/0052; H01L 51/0053; H01L 51/0055; H01L 51/0056; H01L 51/0058; H01L 51/0067; H01L 51/0072; H01L 51/5012; H01L 51/5076; H01L 51/5092; H05B 33/0896

See application file for complete search history.

(56) References Cited

U.S. PATENT DOCUMENTS

| | | |
|---|---|---|
| 2005/0110005 A1 | 5/2005 | Forrest et al. |
| 2010/0051991 A1 | 3/2010 | Shiratori et al. |
| 2010/0327265 A1 | 12/2010 | Kimura et al. |
| 2015/0270493 A1 | 9/2015 | Nishide et al. |

FOREIGN PATENT DOCUMENTS

| | | |
|---|---|---|
| JP | 2010-56211 A | 3/2010 |
| JP | 2010-171230 A | 8/2010 |
| JP | 2011-98948 A | 5/2011 |
| JP | 2014-9220 A | 1/2014 |

ORGANIC LIGHT EMITTING ELEMENT

TECHNICAL FIELD

The present invention relates to an organic light emitting element, a display device, an image information processing device, a lighting device, an image forming device, and an exposing device.

BACKGROUND ART

An organic electroluminescence element (also referred to as "organic EL element") is an electronic element including a pair of electrodes and an organic compound layer placed between the electrodes. An electron and a hole are injected from the pair of electrodes, and the electron and the hole recombine in the organic compound layer. As a result, an exciton of a luminous organic compound is produced and the organic light emitting element emits light when the exciton returns to its ground state.

At least one organic compound layer is placed between the electrodes of an organic light emitting element. Available as one layer constituting the organic compound layer is an electron injection layer that serves to inject and transport an electron injected from a cathode into an emission layer. For example, an alkaline metal or alkaline earth metal derivative has been widely known as a constituent material for the electron injection layer. It is because each of the alkaline metal and alkaline earth metal derivatives is a material having a small work function and shows a good electron injection property that the alkaline metal or alkaline earth metal derivative is used as the constituent material for the electron injection layer. However, it has been known that each of the alkaline metal and alkaline earth metal derivatives is a material that easily reacts with water, and an organic light emitting element including any one of the alkaline metal and alkaline earth metal derivatives as a constituent material for its electron injection layer is affected by moisture in the air. Therefore, at present, the organic light emitting element needs to be stringently sealed so that the organic light emitting element may not be exposed to the moisture in the air. Meanwhile, various researches and developments have been conducted on a method of stably driving the organic light emitting element even in the air except the sealing in order to eliminate an influence of the moisture in the air.

As one method of improving the stability of the organic light emitting element against the moisture in the air, there is known, for example, a method involving introducing Compound a-1 having an electron donor property and Compound a-2 having an electron acceptor property shown below into the electron injection layer like PTL 1.

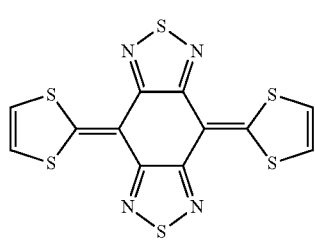

a-1

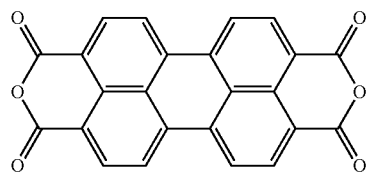

a-2

In the electron injection layer of the organic light emitting element of PTL 1, the compound having an electron donor property (D molecule) donates an electron to the compound having an electron acceptor property (A molecule), whereby charge (an electron) is generated. In addition, a strong interaction occurs between the D molecule and the A molecule, and hence a polarized DA complex is produced. Thus, the organic light emitting element of PTL 1 can perform the injection of an electron.

NPL 1 discloses Viologen Compound b-1 shown below as a compound having a high electron donor property. Viologen Compound b-1 below is a compound that is stable in the air, and is a compound that serves to reduce the work function of a gold electrode.

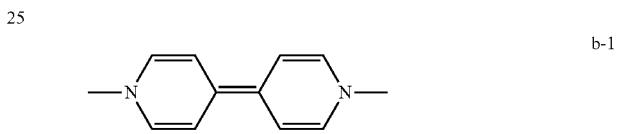

b-1

CITATION LIST

Patent Literature

PTL 1: US Patent Publication No. 2005/0110005

Non Patent Literature

NPL 1: Appl. Phys. Lett. 93, 243303 (2008)

SUMMARY OF INVENTION

Technical Problem

However, the HOMO of Compound a-1 (electron donor-property compound) is deep and hence the energy level of the DA complex to be formed in the organic light emitting element of PTL 1 is deep. Therefore, the use of Compounds a-1 and a-2 as constituent materials for an electron injection layer constituting an organic light emitting element has involved a problem in that a barrier for the injection of an electron into an emission layer is large and hence good light emission is not obtained, though the use enables the acceptance of an electron from an electrode (cathode). In addition, NPL 1 describes that Viologen Compound b-1 has a high electron donor property but the compound has involved a problem in that the compound does not function as the electron injection layer of an organic light emitting element.

The present invention has been made to solve the above-mentioned problems and an object of the present invention is to provide an organic light emitting element having stable performance in the air.

Solution to Problem

An organic light emitting element according to a first embodiment of the present invention includes:

an anode;
a cathode; and
an emission layer placed between the anode and the cathode,
in which:
the organic light emitting element further includes
  a first organic compound layer placed between the cathode and the emission layer, and
  a second organic compound layer placed between the emission layer and the first organic compound layer, and brought into contact with the first organic compound layer;
the first organic compound layer contains a first organic compound;
the second organic compound layer contains a second organic compound;
the first organic compound includes an organic compound represented by the following general formula [1]; and
the second organic compound includes an organic compound different from the first organic compound.

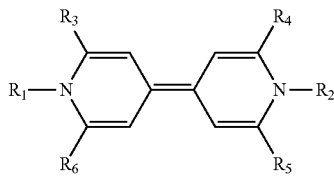

[1]

In the formula [1], $R_1$ to $R_6$ each represent a hydrogen atom or a substituent selected from a fluorine atom, an alkyl group, an alkoxy group, an aryl group and a heteroaryl group; when any one of $R_1$ to $R_6$ represents an alkyl group or an alkoxy group, the alkyl group or the alkoxy group may further have a fluorine atom; and when any one of $R_1$ to $R_6$ represents an aryl group or a heteroaryl group, the aryl group or the heteroaryl group may further have a fluorine atom, an alkyl group, an alkoxy group, or an amino group.

An organic light emitting element according to a second embodiment of the present invention includes:
an anode;
a cathode; and
an emission layer placed between the anode and the cathode,
in which:
the organic light emitting element further includes an organic compound layer placed between the emission layer and the cathode;
the organic compound layer contains a first organic compound and a second organic compound; and
the first organic compound includes an organic compound represented by the following general formula [1]; and
the second organic compound includes an organic compound different from the first organic compound.

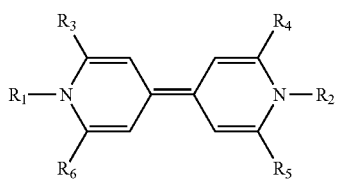

[1]

In the formula [1], $R_1$ to $R_6$ each represent a hydrogen atom or a substituent selected from a fluorine atom, an alkyl group, an alkoxy group, an aryl group and a heteroaryl group; when any one of $R_1$ to $R_6$ represents an alkyl group or an alkoxy group, the alkyl group or the alkoxy group may further have a fluorine atom; and when any one of $R_1$ to $R_6$ represents an aryl group or a heteroaryl group, the aryl group or the heteroaryl group may further have a fluorine atom, an alkyl group, an alkoxy group, or an amino group.

According to the embodiments of the present invention, the organic light emitting element having stable performance in the air can be provided.

DESCRIPTION OF EMBODIMENTS

Figure 1:
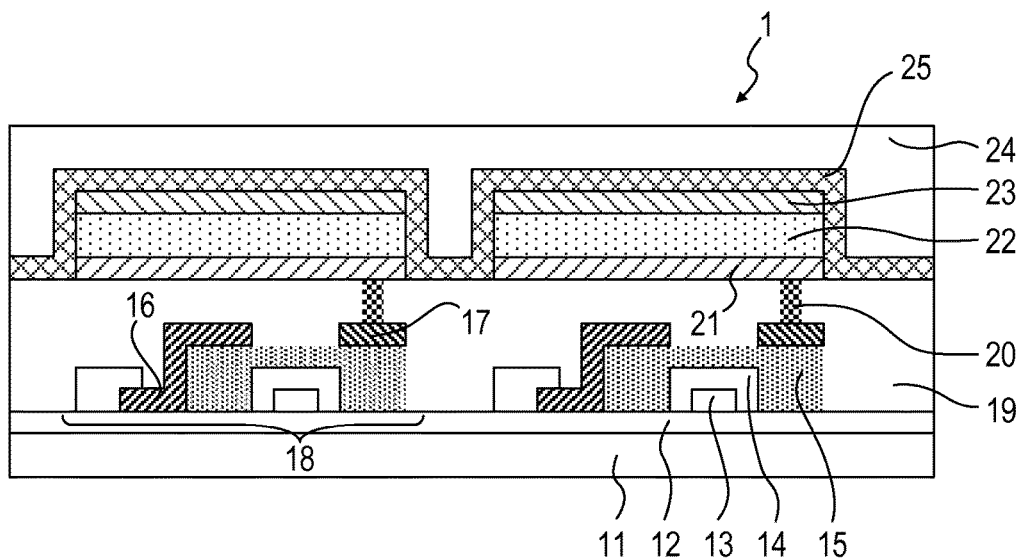
FIG. 1 is a schematic sectional view illustrating an example of a display device including an organic light emitting element of the present invention and an active element connected to the organic light emitting element.

The present invention relates to an organic light emitting element including an anode, a cathode, and an emission layer placed between the anode and the cathode. The organic light emitting element of the present invention includes a first organic compound layer and second organic compound layer described in the following (A), or an organic compound layer described in the following (B).

(A) A first organic compound layer placed between the cathode and the emission layer, and a second organic compound layer placed between the emission layer and the first organic compound layer, and brought into contact with the first organic compound layer (B) An organic compound layer placed between the cathode and the emission layer When the organic light emitting element of the present invention includes the two layers (the first organic compound layer and the second organic compound layer) described in the (A), the first organic compound layer contains a first organic compound and the second organic compound layer contains a second organic compound. In the present invention, the first organic compound is an organic compound represented by the following general formula [1]. Meanwhile, in the present invention, the second organic compound is an organic compound different from the first organic compound.

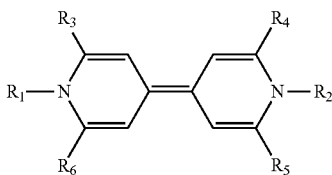

It should be noted that details about the compound represented by the general formula [1] (the first organic compound) and the second organic compound are described later. In addition, when the organic light emitting element of the present invention includes the two layers (the first organic compound layer and the second organic compound layer) described in the (A), the first organic compound layer is preferably a layer brought into contact with the cathode.

In addition, when the organic light emitting element of the present invention includes the organic compound layer described in the (B), the organic compound layer contains a first organic compound and a second organic compound. In the present invention, the first organic compound is an organic compound represented by the general formula [1]. Meanwhile, the second organic compound is an organic compound different from the organic compound represented by the general formula [1]. When the organic light emitting element of the present invention includes the organic compound layer described in the (B) as just described, the organic compound layer is preferably a layer brought into contact with the cathode.

(Organic Light Emitting Element)

A specific construction of the organic light emitting element of the present invention is described below.

In the organic light emitting element of the present invention, at least the emission layer is placed between the anode and the cathode as a pair of electrodes. In the present invention, the emission layer and an electron injection layer as a layer closest to the cathode are preferably placed between the anode and the cathode. However, in the present invention, layers to be placed between the anode and the cathode are not limited to the emission layer and the electron injection layer. In addition to the emission layer and the electron injection layer, a layer such as a hole injection layer, a hole transport layer, a hole blocking layer, an electron transport layer, or an exciton blocking layer may be appropriately introduced.

In addition, in the present invention, for example, an insulating layer, an adhesion layer, or an interference layer may be formed at an interface between an electrode and a layer formed between both the electrodes. Further, when a charge transport layer (an electron transport layer or a hole transport layer) is incorporated as a layer to be formed between both the electrodes, the charge transport layer may be formed of a plurality of layers having different ionization potentials. As described above, the organic light emitting element of the present invention can adopt various layer constructions.

In the present invention, the light extraction construction of the organic light emitting element may be a top emission system in which light is extracted from an electrode on a substrate side, or may be a bottom emission system in which light is extracted from a side opposite to the substrate. A construction in which light is extracted from each of both the sides is also permitted.

(First Organic Compound (Electron Donor-Property Compound))

Next, in the organic light emitting element of the present invention, the first organic compound represented by the following general formula [1] is described. It should be noted that in the present invention, the first organic compound is a compound having an electron donor property, and is used as a constituent material for the organic compound layer placed between the cathode and the emission layer. In the present invention, the organic compound layer is preferably a layer brought into contact with the cathode and is particularly preferably the electron injection layer. In addition, in the following description, the first organic compound represented by the general formula [1] is sometimes referred to as "electron donor-property compound X."

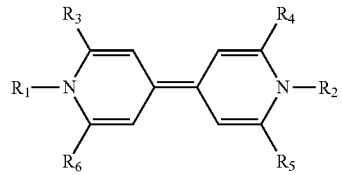

In the formula [1], $R_1$ to $R_6$ each represent a hydrogen atom or a substituent selected from a fluorine atom, an alkyl group, an alkoxy group, an aryl group and a heteroaryl group.

Examples of the alkyl group represented by any one of $R_1$ to $R_6$ include a methyl group, an ethyl group, a n-propyl group, an isopropyl group, a n-butyl group, a tert-butyl group, a n-hexyl group, a n-heptyl group, and a n-octyl group.

The alkyl group represented by any one of $R_1$ to $R_6$ is preferably an alkyl group having 1 to 12 carbon atoms. This is because of the following reason: as the number of carbon atoms of the alkyl group increases, the molecular weight of the entirety of the compound increases by an amount corresponding to the increase, which makes it difficult to subject the compound to sublimation purification. However, the alkyl group has an effect of forming a good amorphous film. In addition, the alkyl group is a substituent having an electron-donating effect and hence the introduction of the group into the electron donor-property compound represented by the general formula [1] can additionally reduce the oxidation potential of the compound itself.

An example of the alkoxy group represented by any one of $R_1$ to $R_6$ is a methoxy group.

The alkoxy group represented by any one of $R_1$ to $R_6$ is preferably an alkoxy group having 1 to 12 carbon atoms. This is because of the same reason as that of the alkyl group. In addition, the alkoxy group is a substituent having an electron-donating effect larger than that of the alkyl group and hence the introduction of the group into the electron donor-property compound represented by the general formula [1] can additionally reduce the oxidation potential of the compound itself.

It should be noted that when any one of $R_1$ to $R_6$ represents an alkyl group or an alkoxy group, the alkyl group or the alkoxy group may further have a fluorine atom. That is, at least part of hydrogen atoms in the alkyl group or the alkoxy group may be substituted with a fluorine atom. The alkyl group or alkoxy group as a substituent at least part of the hydrogen atoms of which are substituted with fluorine as described above exhibits the following effect: by virtue of the hydrophobic effect or oleophobic effect of a fluorine atom, the compound itself has additional difficulty in reacting with moisture or oxygen in the air and is improved in sublimation property.

Examples of the aryl group represented by any one of $R_1$ to $R_6$ include a phenyl group, a biphenyl group, a terphenyl group, a naphthyl group, a phenanthryl group, a fluorenyl group, and substituents shown below.

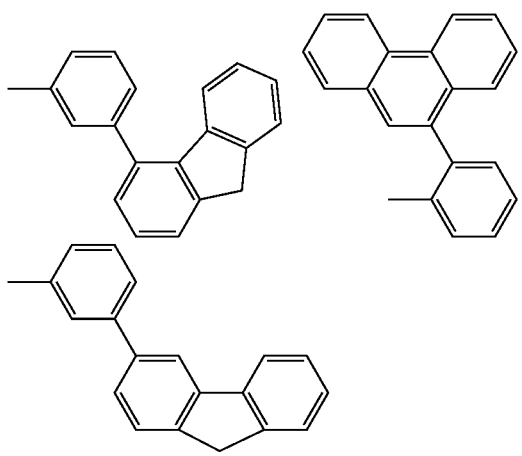

The aryl group represented by any one of $R_1$ to $R_6$ is preferably an aryl group having 6 to 18 carbon atoms. This is because as the molecular weight increases, it becomes more difficult to perform sublimation purification. Examples of the aryl group having 6 to 18 carbon atoms include a phenyl group, a biphenyl group, a terphenyl group, a naphthyl group, a fluorenyl group, and a phenanthryl group.

Examples of the heteroaryl group represented by any one of $R_1$ to $R_6$ include a pyridyl group, a pyrimidyl group, a triazinyl group, a thienyl group, a furyl group, a pyrrolyl group, a phenylpyrrolyl group, an imidazolyl group, a benzimidazolyl group, a triazolyl group, a phenoxazinyl group, a xanthenyl group, and a dibenzofuranyl group.

In addition, when any one of $R_1$ to $R_6$ represents an aryl group or a heteroaryl group, the aryl group or the heteroaryl group may further have a fluorine atom, an alkyl group such as a methyl group, an ethyl group, an isopropyl group, or a tert-butyl group, an alkoxy group such as a methoxy group, or an amino group. It should be noted that in the present invention, when the aryl group or heteroaryl group represented by any one of $R_1$ to $R_6$ further has an amino group, a hydrocarbon skeleton constituting the amino group and the aryl group or the heteroaryl group may further form a fused ring. That is, for example, a substituent represented by the following formula is also included in a substituent represented by any one of $R_1$ to $R_6$.

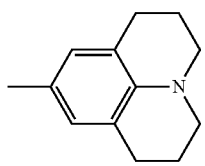

By the way, when a substituent represented by any one of $R_1$ to $R_6$ of the viologen compound represented by the general formula [1] (first organic compound) is appropriately changed, any one of the physical properties of the compound itself, specifically its oxidation potential, film property, heat stability, and sublimation property can be finely adjusted. Here, while the introduction of an electron-donating substituent reduces the oxidation potential, the introduction of an electron-withdrawing substituent increases the oxidation potential. It should be noted that out of the substituents ($R_1$ to $R_6$) in the formula [1], $R_1$ and $R_2$ largely contribute to a change in the oxidation potential.

In the present invention, the organic compound represented by the general formula [1] (electron donor-property compound X) can be used alone as a constituent material for the electron injection layer of the organic light emitting element. However, in the present invention, in addition to the electron donor-property compound X, a compound different from the electron donor-property compound X may be introduced into the electron injection layer. In addition, in the present invention, a layer containing the compound different from the electron donor-property compound X may be formed so as to be brought into contact with the electron injection layer. The compound different from the electron donor-property compound X as used herein includes the second organic compound, and is preferably an electron acceptor-property compound Y to be described below.

(Second Organic Compound (Electron Acceptor-Property Compound))

Next, the second organic compound as a constituent material for an organic compound layer between the emission layer and cathode in the organic light emitting element of the present invention is described. In the present invention, the second organic compound is preferably a compound represented by any one of the following general formulae [3-1] to [3-21], [4-1], and [4-2]. It should be noted that in the following description, the second organic compound is sometimes referred to as "electron acceptor-property compound."

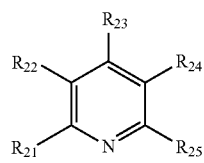
[3-1]

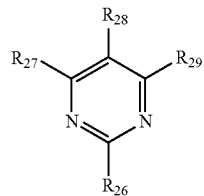
[3-2]

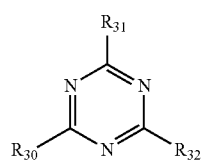
[3-3]

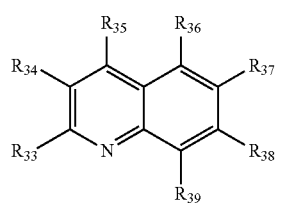
[3-4]

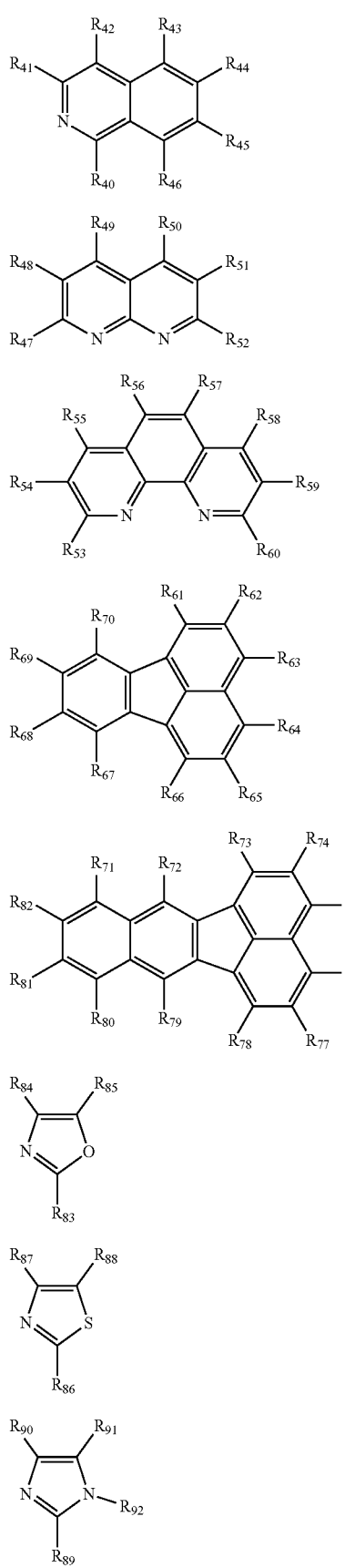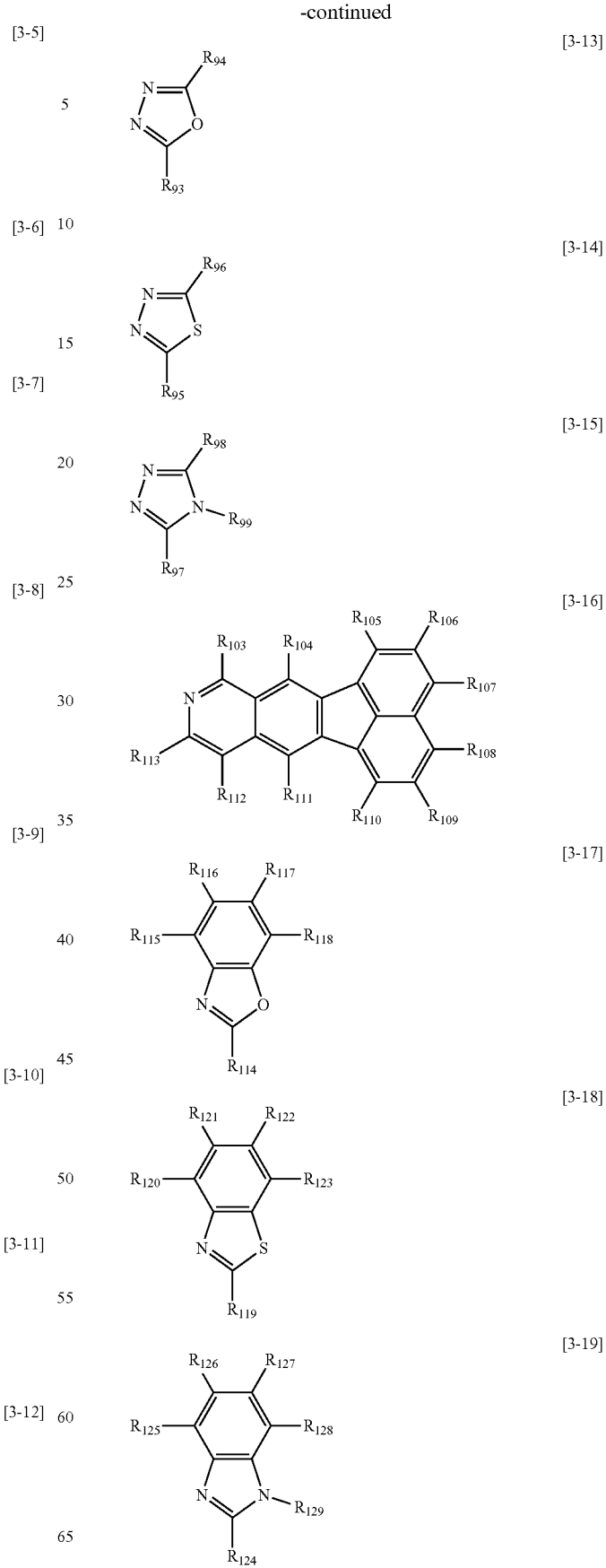

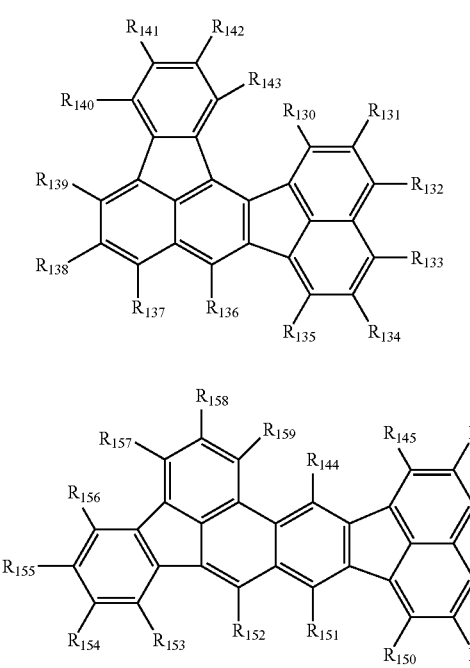
[3-20]

[3-21]

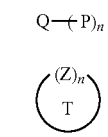

Q—(P)$_n$ [4-1]

[4-2]

In the formulae [3-1] to [3-21], [4-1], and [4-2], $R_{21}$ to $R_{99}$ and $R_{103}$ to $R_{159}$ each represent a hydrogen atom or a substituent selected from an alkyl group, an alkoxy group, an aryl group, a heteroaryl group, and a fluorine atom.

Examples of the alkyl group represented by any one of $R_{21}$ to $R_{99}$ and $R_{103}$ to $R_{159}$ include, but of course not limited to, a methyl group, an ethyl group, a n-propyl group, an isopropyl group, a n-butyl group, a tert-butyl group, a n-hexyl group, a n-heptyl group, and a n-octyl group. The alkyl group represented by any one of $R_{21}$ to $R_{99}$ and $R_{103}$ to $R_{159}$ is preferably an alkyl group having 1 to 12 carbon atoms.

An example of the alkoxy group represented by any one of $R_{21}$ to $R_{99}$ and $R_{103}$ to $R_{159}$ is a methoxy group.

Examples of the aryl group represented by any one of $R_{21}$ to $R_{99}$ and $R_{103}$ to $R_{159}$ include, but of course not limited to, a phenyl group, a biphenyl group, a terphenyl group, a naphthyl group, an anthracenyl group, a fluorenyl group, a phenanthryl group, a benzophenanthryl group, a chrysenyl group, a fluoranthenyl group, and a benzofluoranthenyl group.

Examples of the heteroaryl group represented by any one of $R_{21}$ to $R_{99}$ and $R_{103}$ to $R_{159}$ include, but of course not limited to, a pyridinyl group, a pyrimidinyl group, a triazinyl group, a thienyl group, a furyl group, a pyrrolyl group, an imidazolyl group, and a triazolyl group.

It should be noted that when any one of $R_{21}$ to $R_{99}$ and $R_{103}$ to $R_{159}$ represents an aryl group or a heteroaryl group, the aryl group or the heteroaryl group may further have an alkyl group such as a methyl group, an ethyl group, an isopropyl group and a tert-butyl group, an alkoxy group such as a methoxy group, an aryl group such as a phenyl group, a heteroaryl group such as a pyridyl group, a fluorine atom, or a cyano group.

In the formula [4-1], a unit Q represents a basic structure represented by any one of the formulae [3-1] to [3-21] or a partial structure including an aromatic ring having 6 to 30 carbon atoms. The partial structure including an aromatic ring having 6 to 30 carbon atoms corresponding to the unit Q is, for example, a partial structure defined by any one of the following (A) to (C). However, in the present invention, the partial structure is not limited to the following.

(A) A complex substituent obtained by combining a basic structure represented by any one of the formulae [3-1] to [3-21] and an aryl group (B) A complex substituent obtained by combining a plurality of aryl groups (C) A condensed polycyclic substituent in which 6 or more carbon atoms each having an sp$^2$ hybrid orbital are present (A complex substituent formed of a plurality of partial structures is also included.)

Specific examples of the partial structure corresponding to the unit Q include the following partial structures. However, in the present invention, the partial structure is not limited to the following. It should be noted that in the formulae, * represents a bonding hand with a unit P to be described later.

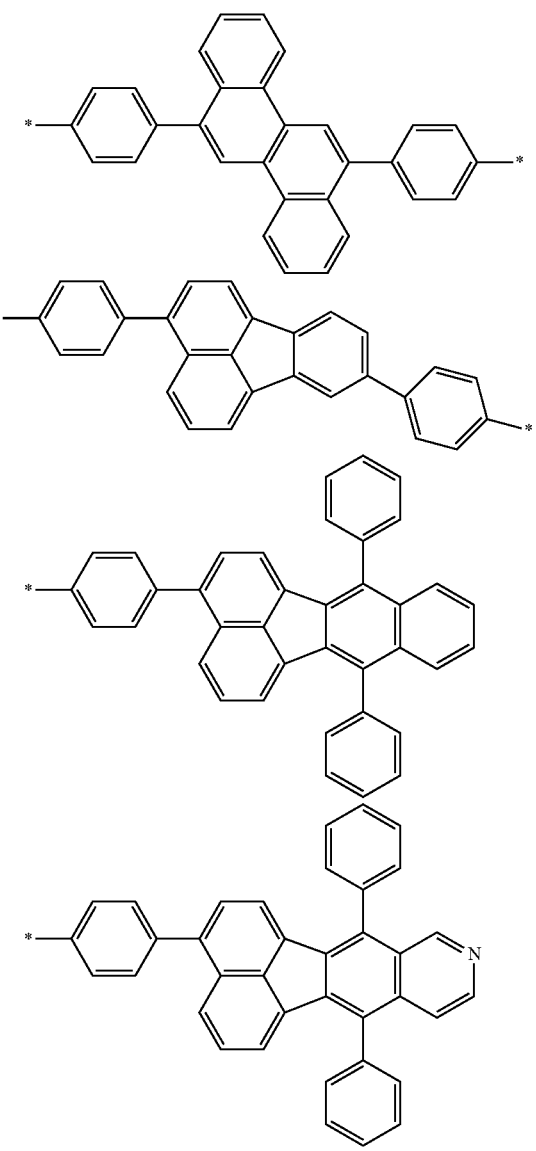

-continued

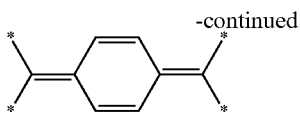

In the formula [4-1], m represents an integer of from 0 to 6.

In the formula [4-1], the unit P represents any one of the following substituents.

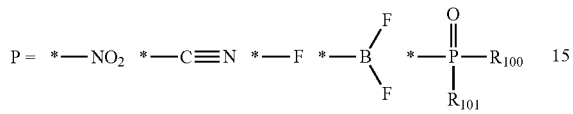

In the formulae, $R_{100}$ and $R_{101}$ each represent a hydrogen atom or a substituent selected from an alkyl group, an alkoxy group, an aryl group, a heteroaryl group, and a fluorine atom. It should be noted that when any one of $R_{100}$ and $R_{101}$ represents an aryl group or a heteroaryl group, the aryl group or the heteroaryl group may further have an alkyl group, an alkoxy group, an aryl group, a heteroaryl group, or a fluorine atom. * represents a bonding hand with the unit Q. It should be noted that specific examples of $R_{100}$ and $R_{101}$ are the same as those of $R_{21}$ to $R_{99}$ and $R_{103}$ to $R_{159}$.

In the formula [3-2], a unit T represents a partial structure including an aromatic ring having 6 to 30 carbon atoms or a partial structure including a five- or six-membered heterocyclic structure formed of a carbon atom and an oxygen atom.

The partial structure including an aromatic ring having 6 to 30 carbon atoms corresponding to the unit T is, for example, a partial structure defined by the following (A) or (B). However, in the present invention, the partial structure is not limited to the following.
(A) A complex substituent obtained by combining a plurality of aryl groups
(B) A condensed polycyclic substituent in which 6 or more carbon atoms each having an sp² hybrid orbital are present (A complex substituent formed of a plurality of partial structures is also included.)

Specific examples of the partial structure corresponding to the unit T include the following partial structures. However, in the present invention, the partial structure is not limited to the following. It should be noted that in the formulae, ★ represents a bonding hand with a unit T to be described later.

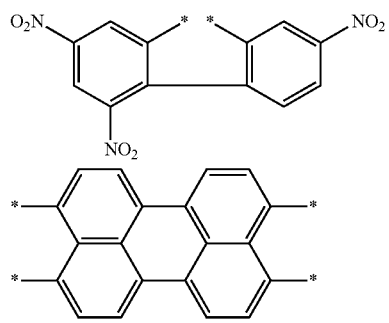

In the formula [4-2], n represents an integer of from 0 to 6.

In the formula [4-2], the unit Z represents any one of the following substituents.

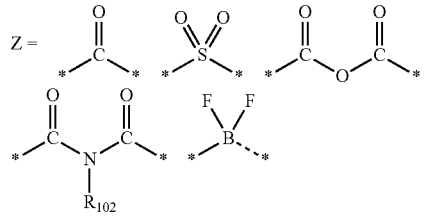

In the formula, $R_{102}$ represents a hydrogen atom or a substituent selected from an alkyl group, an alkoxy group, an aryl group, a heteroaryl group, and a fluorine atom. It should be noted that when $R_{102}$ represents an aryl group or a heteroaryl group, the aryl group or the heteroaryl group may further have an alkyl group, an alkoxy group, an aryl group, a heteroaryl group, or a fluorine atom. ★ represents a bonding hand with the unit T. It should be noted that specific examples of $R_{102}$ are the same as those of $R_{21}$ to $R_{99}$ and $R_{103}$ to $R_{159}$.

A compound represented by any one of the general formulae [3-1] to [3-21] is an electron-deficient condensed ring compound. The electron-deficient condensed ring compound preferably functions as an electron acceptor because a π-electron of a condensed ring serving as a basic skeleton is deficient with respect to a benzene ring. Examples of the electron-deficient condensed ring compound include a pyridine compound (formula [3-1]), a pyrimidine compound (formula [3-2]), a triazine compound (formula [3-3]), a quinoline compound (formula [3-4]), a naphthyridine compound (formula [3-6]), a phenanthroline compound (formula [3-7]), a fluoranthene compound (formula [3-8]), oxazole compounds (formulae [3-10] and [3-17]), triazole compounds (formulae [3-11] and [3-18]), imidazole compounds (formulae [3-12] and [3-19]), an oxadiazole compound (formula [3-13]), a thiadiazole compound (formula [3-14]), and a triazole compound (formula [3-15]). However, the electron-deficient condensed ring compound is not limited to those compounds and a compound formed by condensing a benzene ring or the like to any one of those compounds (the formula [3-5], [3-9], [3-16], [3-20], or [3-21]) can also be used as the electron-deficient condensed ring compound. Of course, the compound is not limited to the foregoing and a compound to be used in an electron transport layer is also permitted.

Each of the compounds represented by the general formulae [4-1] and [4-2] is a compound having an electron-withdrawing substituent. Here, the electron-withdrawing substituent increases the dipole moment of the entire molecule of the compound because the electron-withdrawing force of the substituent itself causes polarization in the molecule. Accordingly, the compound preferably functions as an electron acceptor. Examples of the electron-withdrawing substituent include, but not limited to, a substituent corresponding to the unit P (a nitro group, a cyano group, a fluorine atom, a boron fluoride group, a phosphonyl group, or a monovalent fluorinated alkyl group), and a substituent corresponding to the unit Z (such as a carbonyl group, a sulfonyl group, an anhydride group, an imide group, a boron fluoride group, or a di- or higher valent fluorinated alkyl group).

In the present invention, when an organic compound layer containing the first organic compound (electron donor-property compound) and the second organic compound (electron acceptor-property compound) is formed between the cathode and the emission layer, a mixing ratio between both the compounds in the organic compound layer is preferably adjusted in an appropriate manner. Specifically, the content of the second organic compound (electron acceptor-property compound) in the organic compound layer is preferably more than 0 wt % and 80 wt % or less with respect to the total of the first organic compound (electron donor-property compound) and the second organic compound.

(Relationship Between Electron Donor-Property Compound and Electron Acceptor-Property Compound)

In the present invention, the effect of the present invention is exhibited by incorporating the electron donor-property compound and the electron acceptor-property compound into the electron injection layer constituting the organic light emitting element. It should be noted that the electron injection layer may have a laminated structure formed of the electron donor-property compound X and the electron acceptor-property compound Y, or may be a mixed layer formed of the electron donor-property compound X and the electron acceptor-property compound Y. In addition, in the present invention, the electron donor-property compound X (first organic compound) and the electron acceptor-property compound Y (second organic compound) satisfy the formula [2].

$$|V_{red}-V_{ox}| \leq 1.0 \text{ V} \quad [2]$$

In the formula [2], $V_{red}$ represents the first reduction potential value of the electron acceptor-property compound Y and $V_{ox}$ represents the first oxidation potential value of the electron donor-property compound X. It should be noted that the $V_{red}$ and the $V_{ox}$ are oxidation-reduction potentials obtained by cyclic voltammetry (CV) under the same measurement conditions. Here, the term "the same measurement conditions" means that a solvent, an electrolyte, a working electrode, a reference electrode, a counter electrode, a temperature, and a concentration are kept unchanged. In addition, in the measurement and evaluation of the oxidation-reduction potentials, the half-wave potential value ($E_{1/2}$) of an oxidation-reduction wave that has been generally used is used.

Further, in the present invention, the electron donor-property compound X and the electron acceptor-property compound Y preferably satisfy the formula [5].

$$|V_{red}-V_{ox}| \leq 0.5 \text{ V} \quad [5]$$

By the way, the electron injection layer constituting the organic light emitting element is required to have at least characteristics (i) and (iii) out of the three characteristics listed below.

(i) An ability to accept an electron from the cathode (or an ability to donate a hole to the cathode)
(ii) An ability to transport charge (an electron) (in the layer)
(iii) An ability to inject an electron into an organic compound layer positioned on a side opposite to the cathode (such as an electron transport layer, a hole blocking layer, or the emission layer)

Unless the layer has at least the characteristics (i) and (iii) out of the characteristics (i) to (iii), an electron injected from the cathode cannot be injected into the emission layer and hence good light emission from the emission layer is not obtained. It should be noted that an electron injection layer using an alkali metal or an alkaline earth metal, or a derivative thereof as its constituent material has all the characteristics (i) to (iii) but is not preferred because the electron injection layer easily reacts with a component in the air, especially water to result in its alteration.

The organic light emitting element disclosed in PTL 1 also contains an electron donor-property compound and an electron acceptor-property compound in its electron injection layer but does not provide good light emission. The reason for the foregoing is described below.

In general, there is a large energy barrier between a cathode and an organic compound layer (such as an electron transport layer, a hole blocking layer, or an emission layer). The HOMO of the electron donor-property compound (Compound a-1) disclosed in PTL 1 and the LUMO of the electron acceptor-property compound (Compound a-2) disclosed therein are each −4.5 eV, which is substantially equal to the work function (4.3 eV) of aluminum that has been generally used as a cathode. Therefore, an energy barrier with respect to, for example, the LUMO (−3.3 eV) of $Alq_3$ that has been normally used as a light emitting material in an organic light emitting element enlarges. Accordingly, even when the DA complex described in PTL 1 is introduced into a layer (an electron transport layer or an electron injection layer) having an electron injection/transport property constituting an organic light emitting element, a voltage needed for driving the element increases, and as a result, good light emission from its emission layer is not obtained.

In contrast, the electron donor-property compound X (viologen compound) to be used as a constituent material for the electron injection layer in the organic light emitting element of the present invention has the following advantages: the compound has a high electron donor property, has a low first oxidation potential, and has a shallow HOMO (in a direction approaching a vacuum level).

Here, the following compounds are considered from the viewpoint of an oxidation-reduction potential on the assumption that there is a correlation between a first oxidation potential and a HOMO, and there is also a correlation between a first reduction potential and a LUMO.

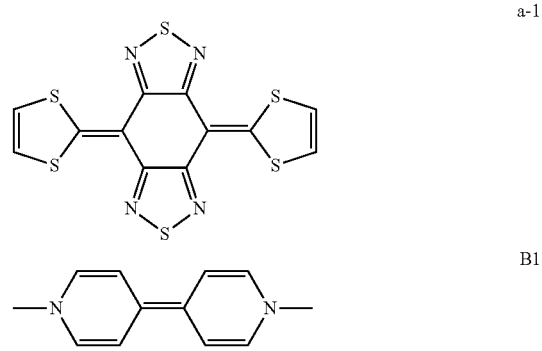

The compounds were subjected to CV measurement under the same conditions. As a result, the first oxidation potentials of Compound a-1 and Compound B1 were 0.3 V and −1.2 V, respectively. The foregoing shows that Compound B1 has a higher electron donor property because the first oxidation potential of Compound B1 is smaller than that of Compound a-1 by 1.5 V. Therefore, when the viologen compound represented by the general formula [1] is adopted as an electron donor-property compound to establish a state in which a DA complex is formed in the electron injection layer, the ability to inject an electron into the organic compound layer (such as the electron transport layer, the hole blocking layer, or the emission layer) increases. As a result, good light emission from the emission layer is obtained.

By the way, NPL 1 describes that when a viologen compound typified by Compound B1 shown above is caused to adhere to the surface of gold so as to have a small thickness (e.g., 0.5 Å), the work function of gold reduces. However, even when a thin film formed of Compound B1 is formed as the electron injection layer of an organic light emitting element so as to have a thickness of the order of less than $10^{-10}$ m (e.g., a thickness of 0.5 Å), good light emission is not obtained from its emission layer. This is probably because the thin film formed of Compound B1 does not function as a layer constituting the organic light emitting element (in the first place, the layer itself is not formed without any defect). The foregoing results from the fact that the diameter of $sp^2$ carbon is generally calculated to be about 1.4 Å and hence a thickness of 0.5 Å is a size order smaller than the diameter of $sp^2$ carbon.

On the other hand, in the organic light emitting element of the present invention, the mixed film containing the electron donor-property compound X (viologen compound) or the laminated film of the electron donor-property compound X and the electron acceptor-property compound Y is formed as the electron injection layer so as to have a thickness order to be typically adopted. The term "thickness order" as used herein specifically refers to a thickness of the order of 0.5 nm or more. Accordingly, the formed mixed film can be said as follows: a thin film formed of Compound B1 functions as a layer constituting the organic light emitting element.

In the organic light emitting element of the present invention, the electron injection layer includes: a mixed film formed of the electron donor-property compound X (viologen compound) and the electron acceptor-property compound Y; and a laminated film obtained by laminating the electron donor-property compound X (viologen compound) and the electron acceptor-property compound Y. Accordingly, in any case, the transfer of charge from the electron donor-property compound X to the electron acceptor-property compound Y or the production of a DA complex polarized by a strong interaction between both the compounds occurs. Here, such interaction occurs between the HOMO of the electron donor-property compound X and the LUMO of the electron acceptor-property compound Y. In addition, in the case where the electron injection layer has a laminated structure, charge occurs between the electron acceptor-property compound and the electron donor-property compound, and hence an electron is easily accepted from the electrode (cathode). On the other hand, in the case of a mixed layer, the DA complex has a carrier and hence the charge mobility of the layer itself increases. Therefore, the electron injection layer constituting the organic light emitting element of the present invention is excellent in electron transport ability as well as in electron injection ability.

In addition, with regard to the relationship of the DA complex, it has been generally known that as the oxidation potential of the electron donor-property compound X and the reduction potential of the electron acceptor-property compound Y become closer to each other, a stronger interaction occurs between the D and A molecules.

Therefore, specifically, as represented by the general formula [2], the potential difference ($|V_{red}-V_{ox}|$) obtained by CV measurement is preferably within 1.0 V. The potential difference is more preferably within 0.5 V as represented by the general formula [5]. This is because additionally reducing the potential difference additionally strengthens the interaction between the D and A molecules.

In the present invention, a mixing ratio between the electron donor-property compound X (viologen compound) and electron acceptor-property compound Y in the electron injection layer is not particularly limited because the two components only need to be mixed in the electron injection layer. For example, the ratio "compound X:compound Y" may be 1:100, the ratio "compound X:compound Y" may be 100:1, or the ratio "compound X:compound Y" may be 50:50. It should be noted that an optimum value for the mixing ratio varies depending on a combination of the compound X and the compound Y, and the kind of a layer or electrode brought into contact with the electron injection layer constituting the organic light emitting element.

As is understood from the foregoing description, in the present invention, when the laminated film or mixed film of the electron donor-property compound X (viologen compound) and the electron acceptor-property compound Y is adopted as the electron injection layer, an electron can be satisfactorily injected from an electrode (cathode) and an electron can be efficiently transported.

By the way, an organic compound having a high electron donor property and a small first oxidation potential generally tends to be readily oxidized in the air. However, the viologen compound to be used as the electron donor-property compound X is a compound that stably exists without being quickly oxidized even in the air. Therefore, the organic light emitting element of the present invention is stable even against a factor involved in the deterioration of the organic light emitting element such as oxygen in the air despite the fact that the element contains the compound having a high electron donor property.

(Specific Examples of Electron Donor-Property Compound)

Specific examples of the electron donor-property compound (viologen compound) to be used as a constituent material for the organic light emitting element of the present invention are shown below. However, the present invention is not limited to these specific examples.

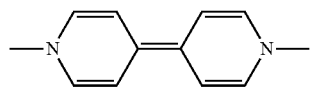

B1

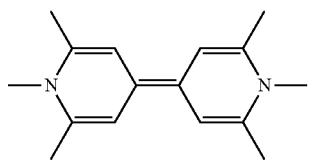

B2

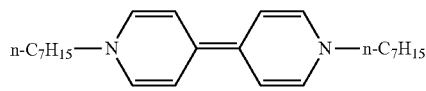

B3

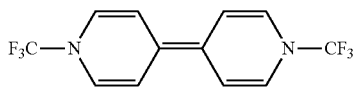

B4

-continued
B5
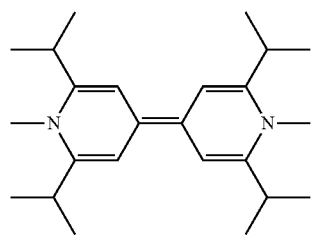
B6
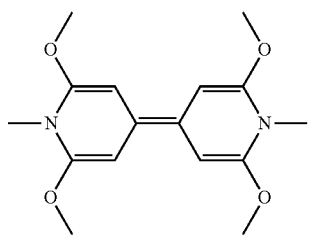
B7
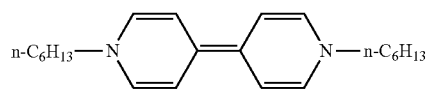
B8
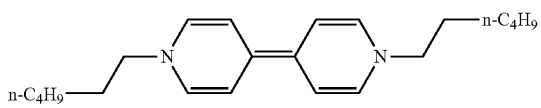
B9
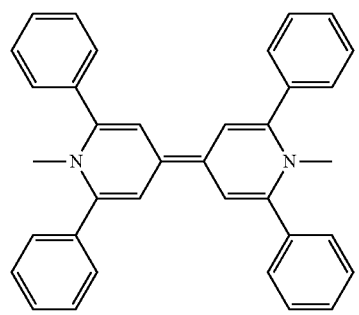
B10
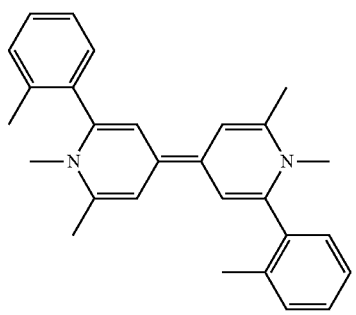
B11
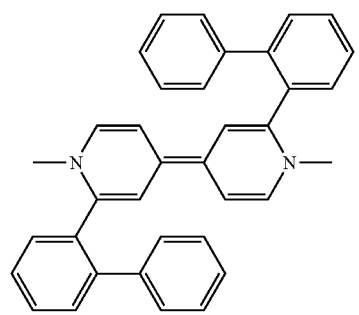
B12
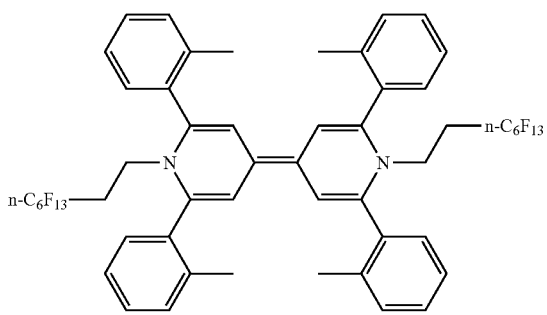
B13
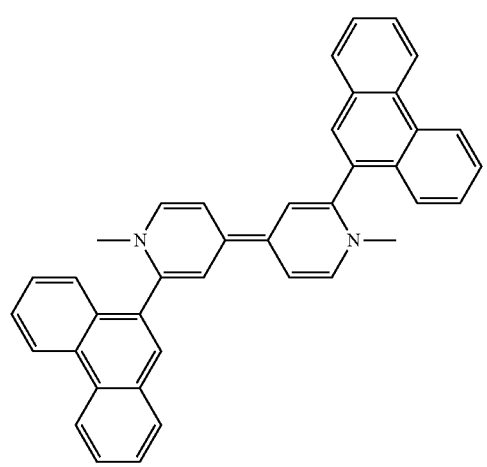
B14
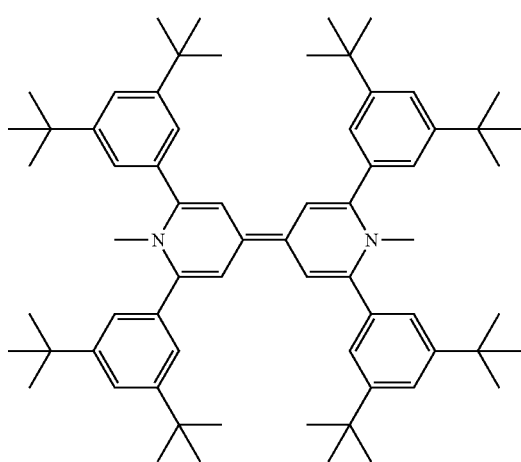

-continued
B15 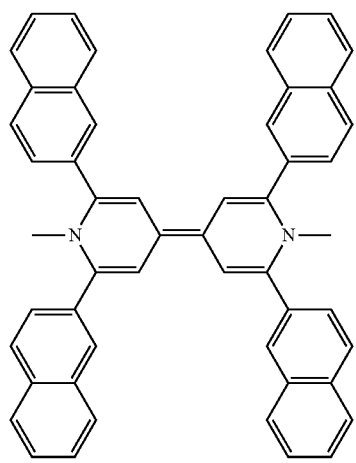
B16 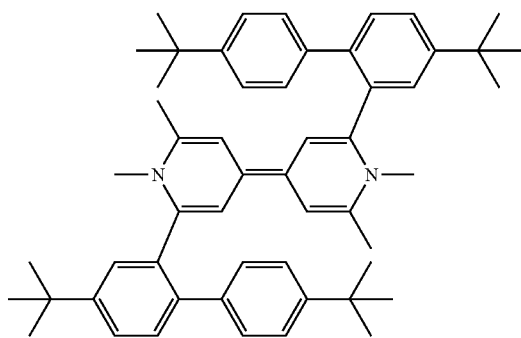
B17 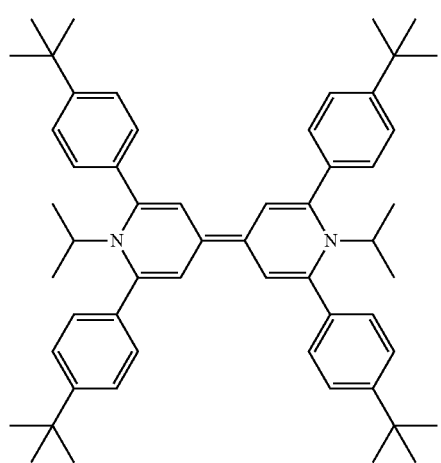
C1 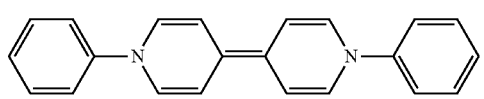
C2 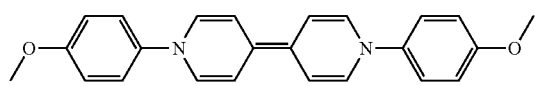
C3 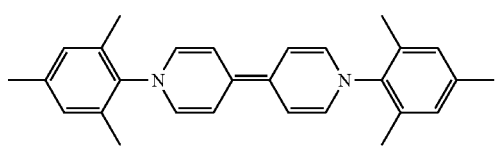
C4 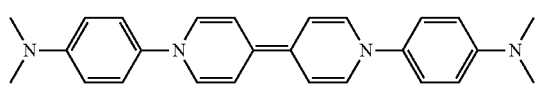
C5 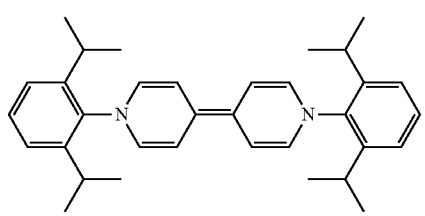
C6 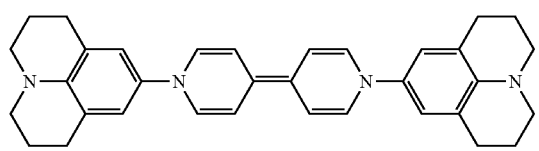
C7 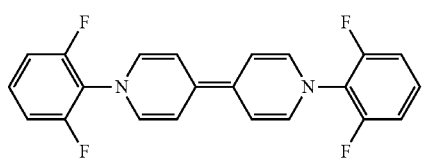

-continued
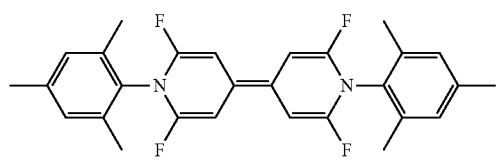 C8
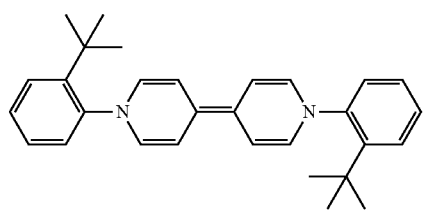 C9
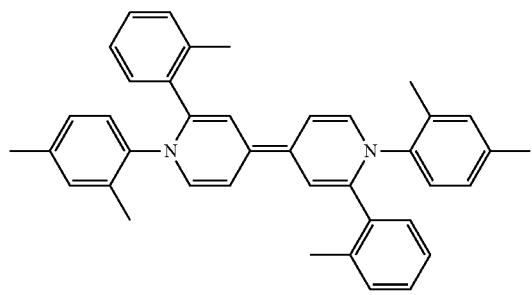 C10
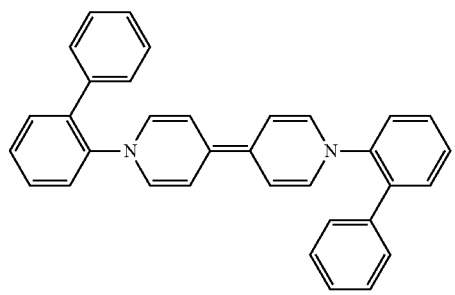 C11
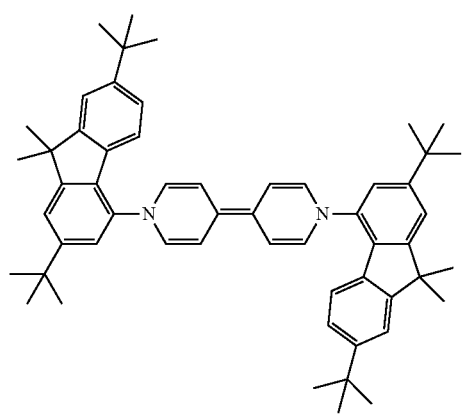 C12
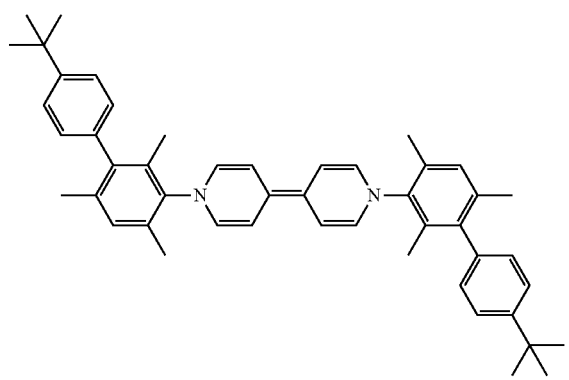 C13
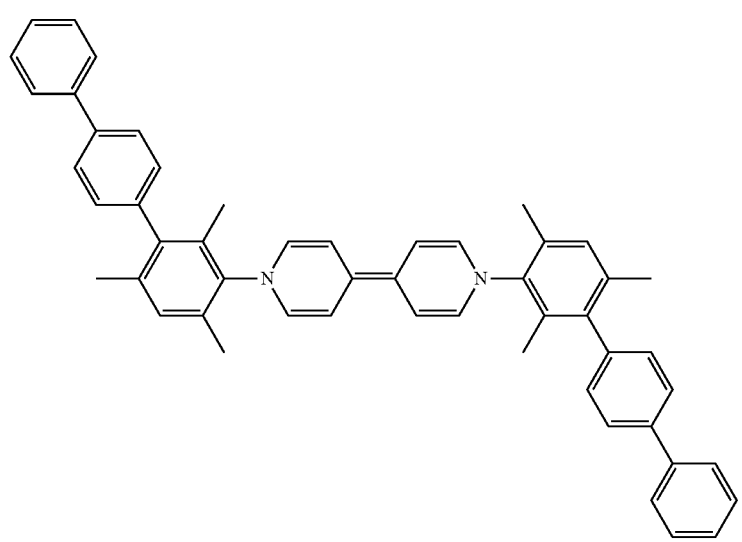 C14

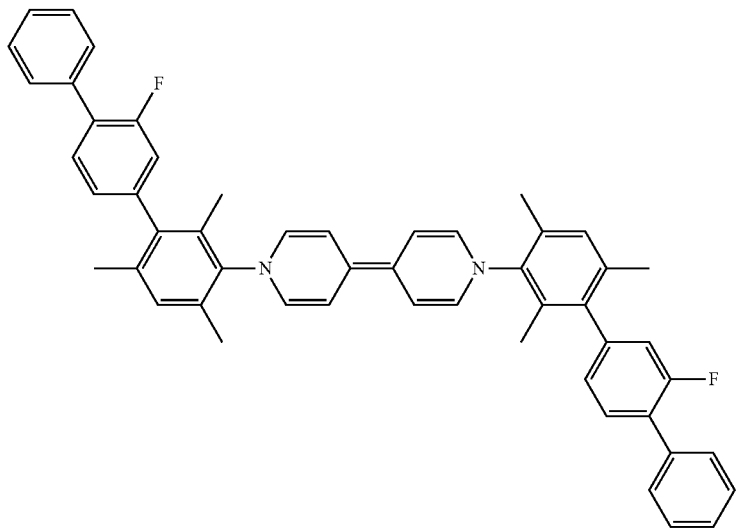
C15
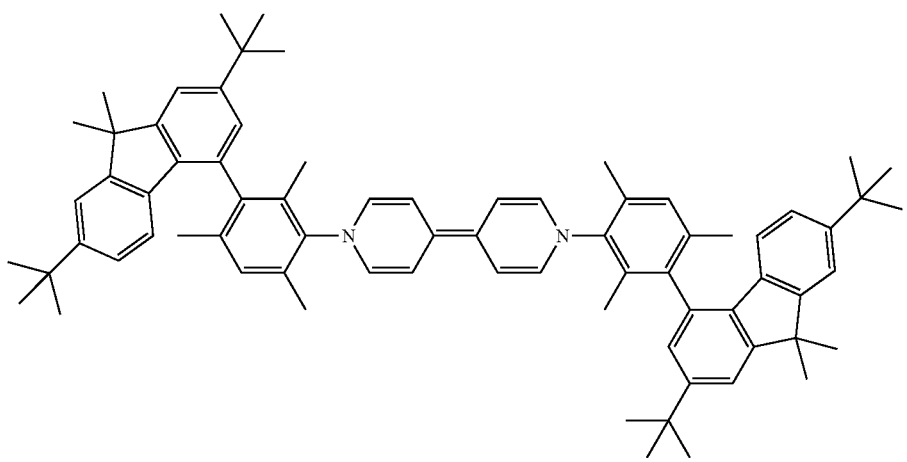
C16
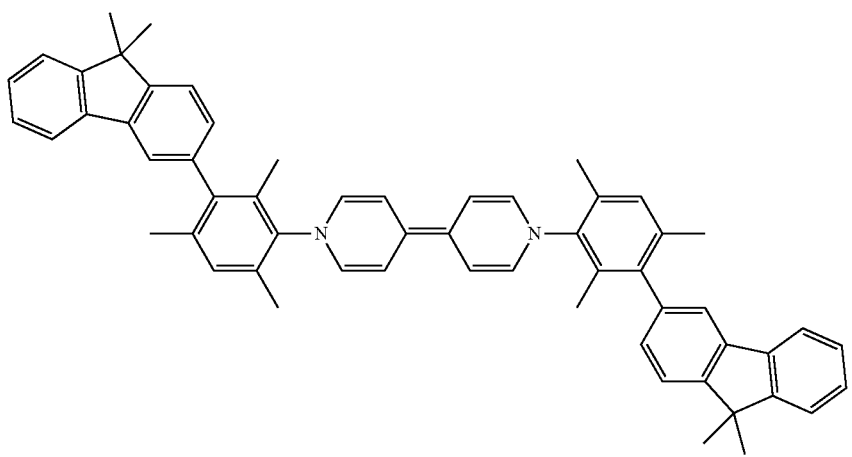
C17

-continued
C18
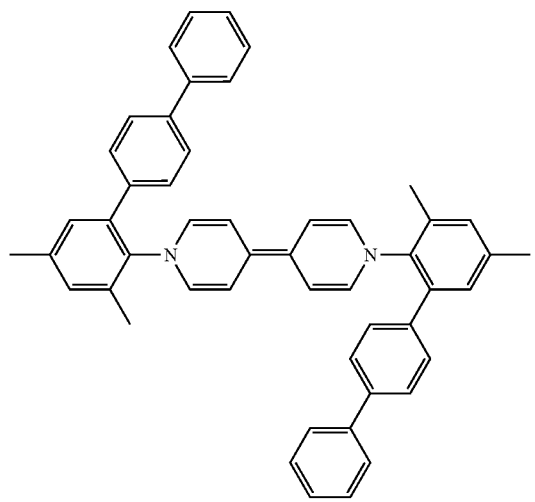
C19
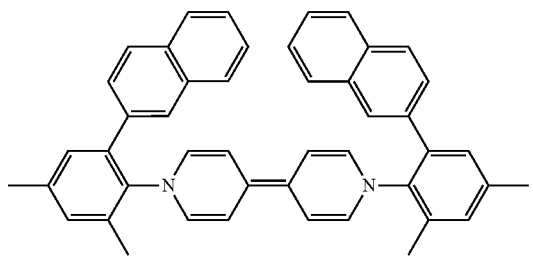
C20
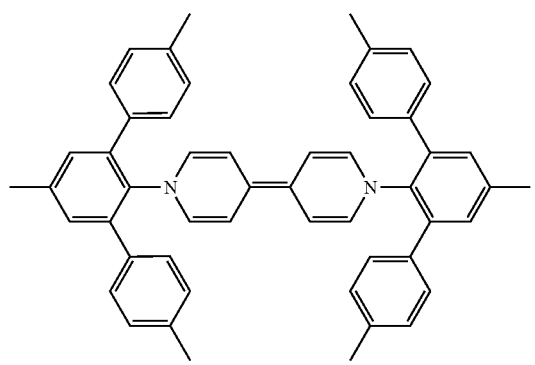
C21
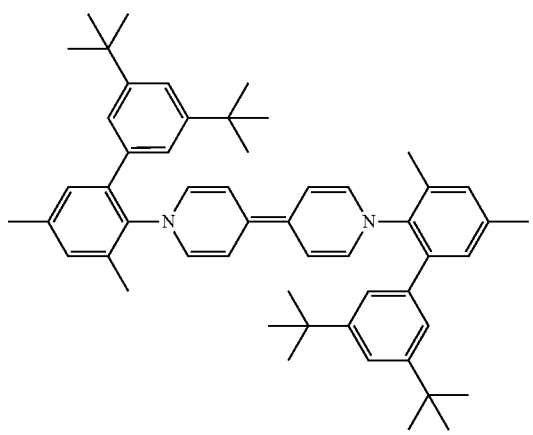
C22
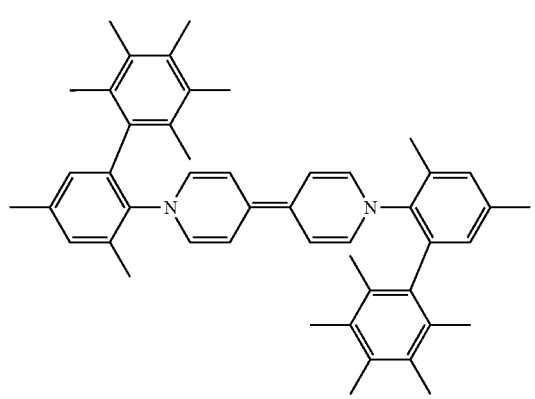
C23
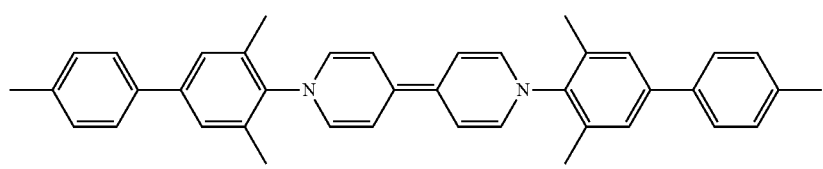

-continued
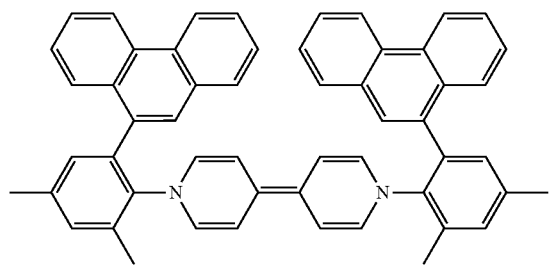
C24
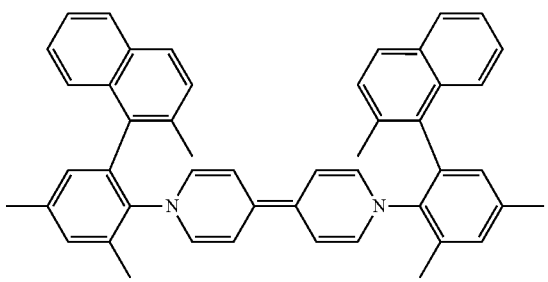
C25
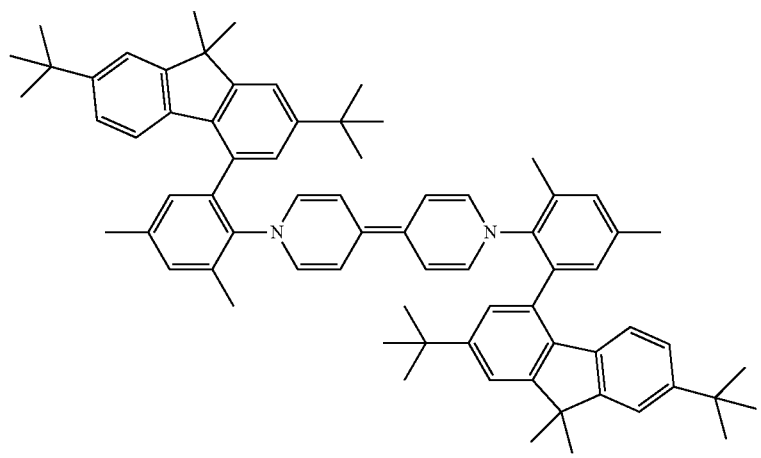
C26
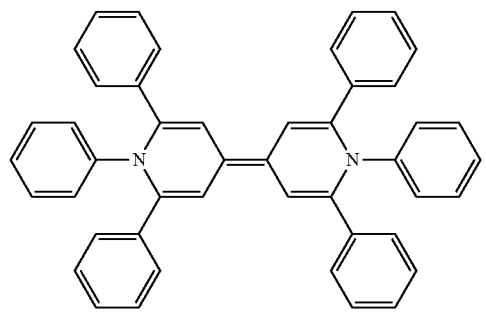
C27
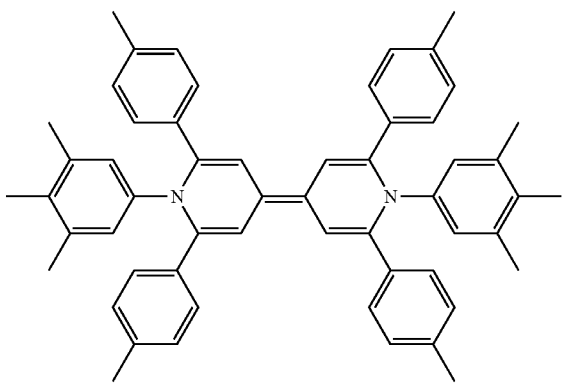
C28
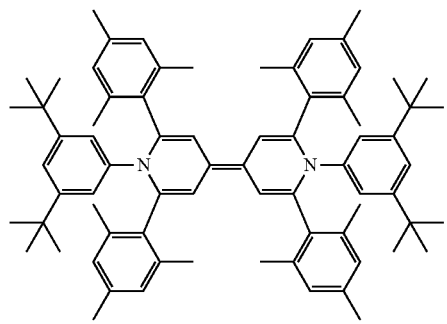
C29
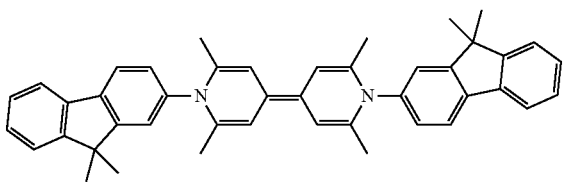
C30

-continued
C31
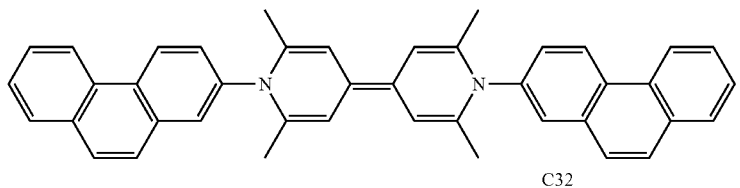
C32
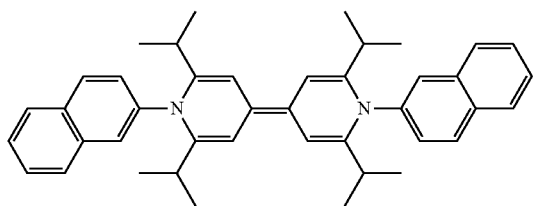
D1
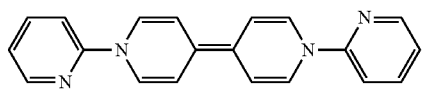
D2
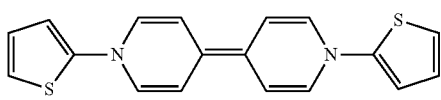
D3
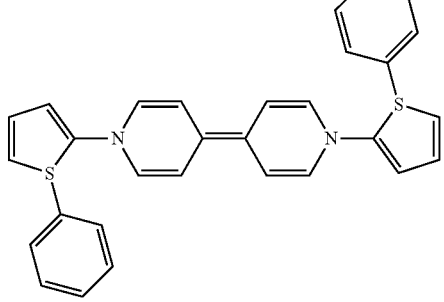
D4
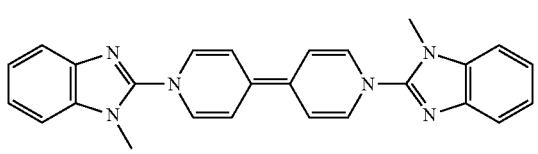
D5
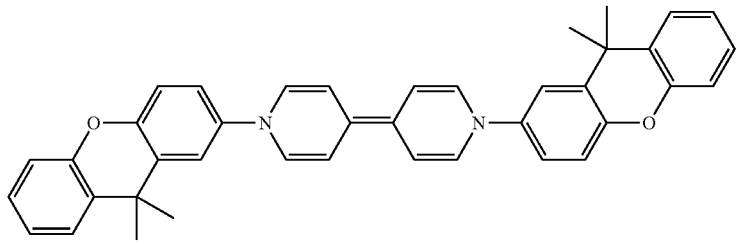
D6
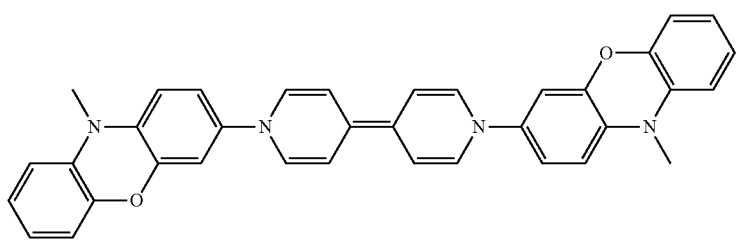
D7
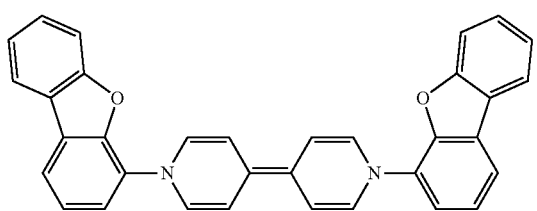
D8
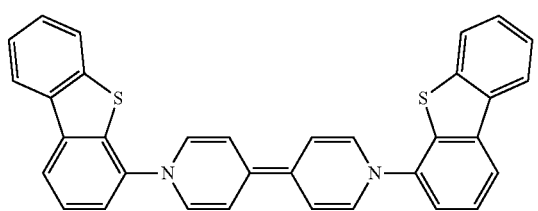

(Properties of Exemplified Compounds)

The compounds listed as the specific examples of the electron donor-property compound X are described below.

By the way, any one of the physical properties of the electron donor-property compound X itself, specifically its oxidation potential, film property, heat stability, and sublimation property can be finely adjusted depending on the kinds and number of substituents to be introduced into a viologen skeleton as the basic skeleton of the compound. Those physical properties can be appropriately selected depending on use purposes.

Each of the exemplified compounds is a compound having a high electron donor property because all the compounds have viologen basic skeletons. Accordingly, a compound that improves stability against the air is preferred. In the present invention, in particular, the following two kinds of compounds are given as a group of compounds that improve stability against the air. It should be noted that the compound represented by the following general formula [6] includes compounds belonging to the C group or the D group out of the listed exemplified compounds, and the compound represented by the following general formula [7] includes the compounds belonging to the B group out of the listed exemplified compounds.

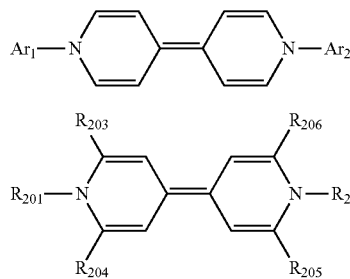

[6]

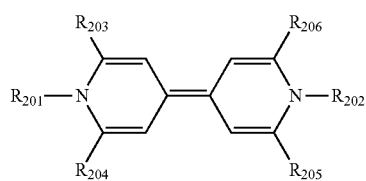

[7]

In the general formula [6], $Ar_1$ and $Ar_2$ each represent an aryl group.

Examples of the aryl group represented by $Ar_1$ or $Ar_2$ include a phenyl group, a biphenyl group, a terphenyl group, a naphthyl group, an anthracenyl group, a fluorenyl group, a phenanthryl group, a benzophenanthryl group, a chrysenyl group, and a fluoranthenyl group.

In addition, the aryl group may further have a fluorine atom, an alkyl group such as a methyl group, an ethyl group, an isopropyl group, or a tert-butyl group, an alkoxy group such as a methoxy group, or an amino group.

The compound represented by the general formula [6] is preferred because of the following reason: the planarity of its viologen main skeleton is improved and the intermolecular stacking property of the compound is improved by substituting the main skeleton with an aryl group having a high stacking effect as a substituent, and hence the penetration of the air can be suppressed.

In the general formula [7], $R_{201}$ to $R_{206}$ each represent a substituent selected from a fluorine atom, an alkyl group, an alkoxy group, and an aryl group.

Examples of the alkyl group represented by any one of $R_{201}$ to $R_{206}$ include a methyl group, an ethyl group, a n-propyl group, an isopropyl group, a n-butyl group, and a tert-butyl group.

An example of the alkoxy group represented by any one of $R_{201}$ to $R_{206}$ is a methoxy group.

Examples of the aryl group represented by any one of $R_{201}$ to $R_{206}$ include a phenyl group, a biphenyl group, a terphenyl group, a naphthyl group, an anthracenyl group, a fluorenyl group, a phenanthryl group, a benzophenanthryl group, a chrysenyl group, and a fluoranthenyl group.

In addition, the aryl group may further have a fluorine atom, an alkyl group such as a methyl group, an ethyl group, an isopropyl group, or a tert-butyl group, an alkoxy group such as a methoxy group, or an amino group.

In the compound represented by the general formula [7], a carbon atom bonded to a nitrogen atom of its viologen skeleton is substituted with any one of a fluorine group, an alkyl group, an alkoxy group, and an aryl group as substituents each having high hydrophobicity. Such substitution is preferred because a substitution position that is liable to be oxidized is capped and hence the oxidation of the compound can be suppressed. This is because nitrogen of a tertiary amine has a high electron-donating property and the reactivity of an $sp^2$ carbon atom that has additionally received the effect improves.

In addition, out of the compounds each represented by the general formula [7], a compound represented by the following general formula [8] is preferred.

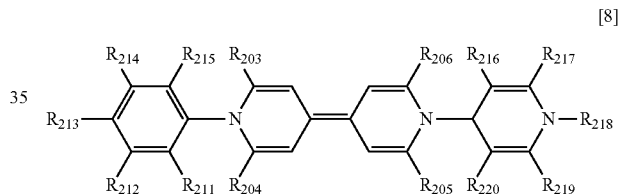

[8]

In the general formula [8], all of $R_{203}$ to $R_{206}$ represent aryl groups, and $R_{211}$ to $R_{220}$ each represent a hydrogen atom or a substituent selected from a fluorine atom, an alkyl group, an alkoxy group, and an aryl group.

It should be noted that the aryl group may further have a fluorine atom, an alkyl group such as a methyl group, an ethyl group, an isopropyl group, or a tert-butyl group, an alkoxy group such as a methoxy group, or an amino group.

When all of $R_{203}$ to $R_{206}$ represent aryl groups as represented by the general formula [8], $R_{201}$ and $R_{202}$ in the general formula [7] each preferably represent a phenyl group. This is because of the following reason: when all of $R_{203}$ to $R_{206}$ represent aryl groups, the molecular weight of the compound increases and the compound becomes sterically bulky, and hence $R_{201}$ and $R_{202}$ in the general formula [7] each preferably represent a phenyl group, which is smallest among the aryl groups, from the viewpoints of sublimation purification and steric bulkiness.

(Specific Examples of Electron Acceptor-Property Compound)

Specific examples of the electron acceptor-property compound to be used as a constituent material for the organic light emitting element of the present invention are shown below. However, the present invention is not limited to these specific examples.

E1
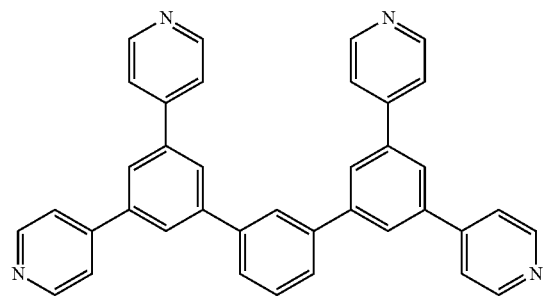
E2
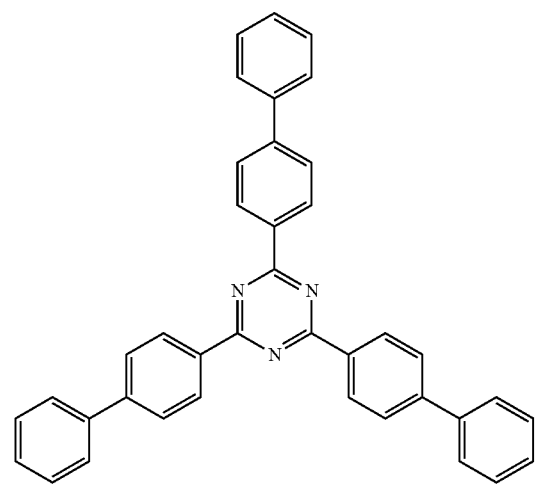
E3
E4
E5
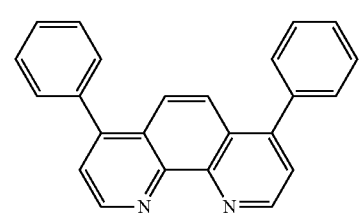
E6
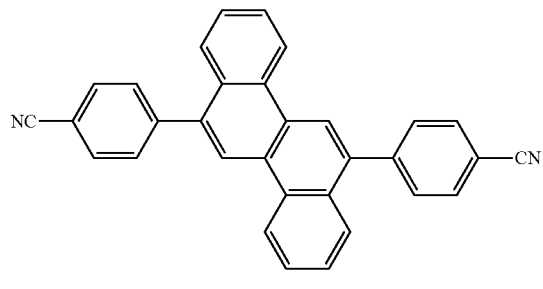
E7
E8
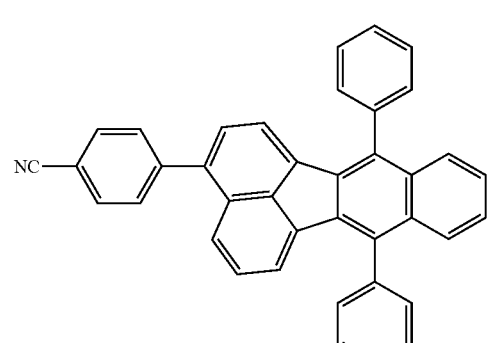
E9
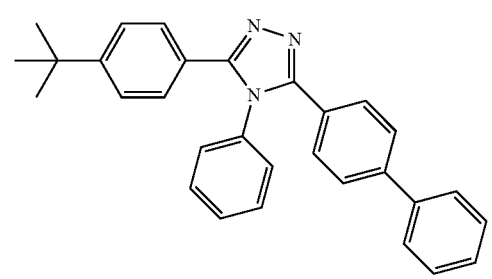
E10
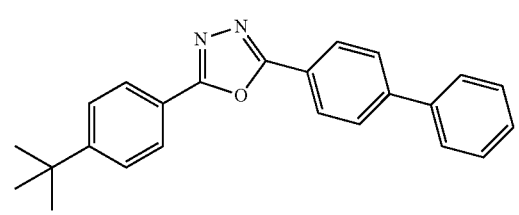
E11
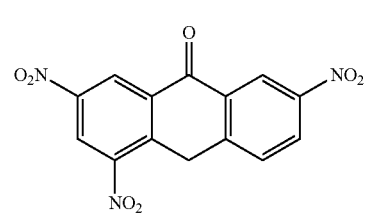

-continued
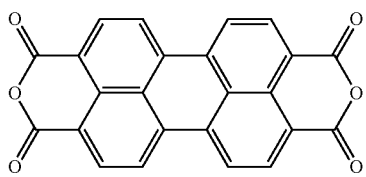
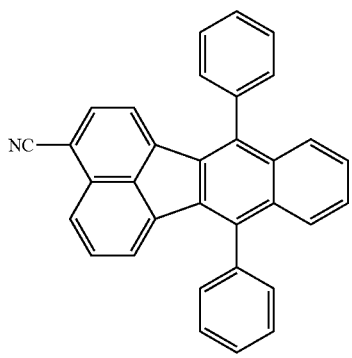
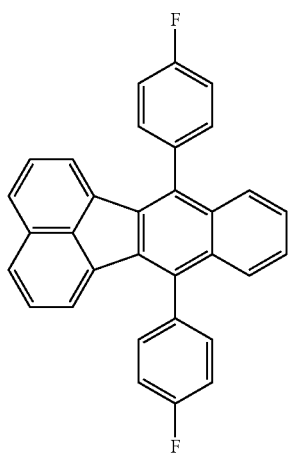
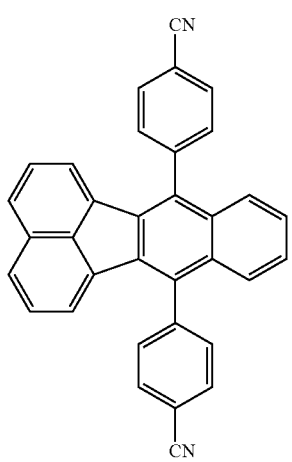
-continued
E12
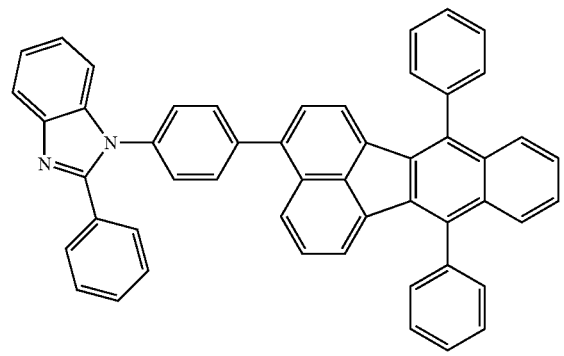
E13
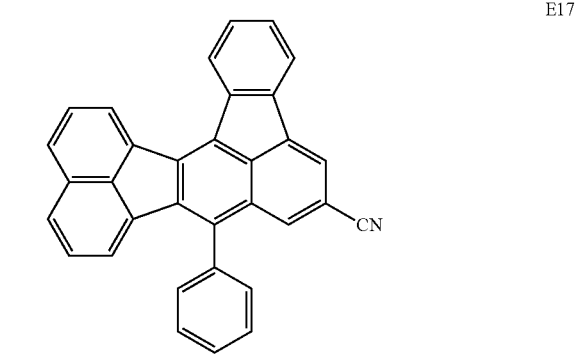
E14
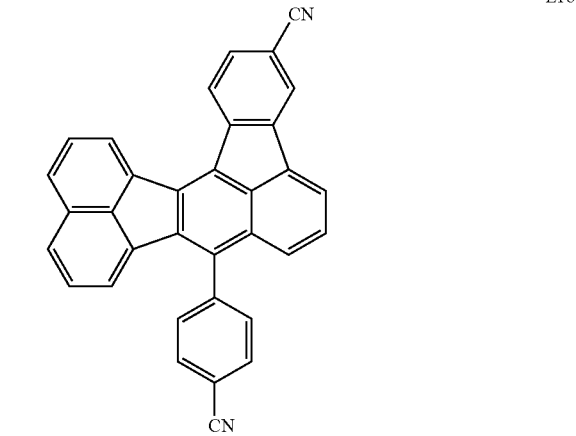
E15
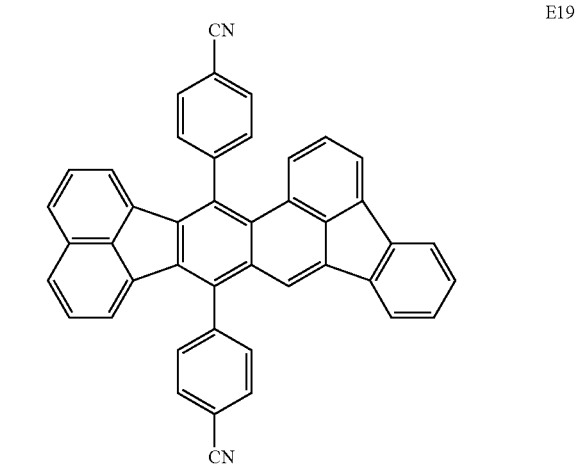
E16
E17
E18
E19

-continued

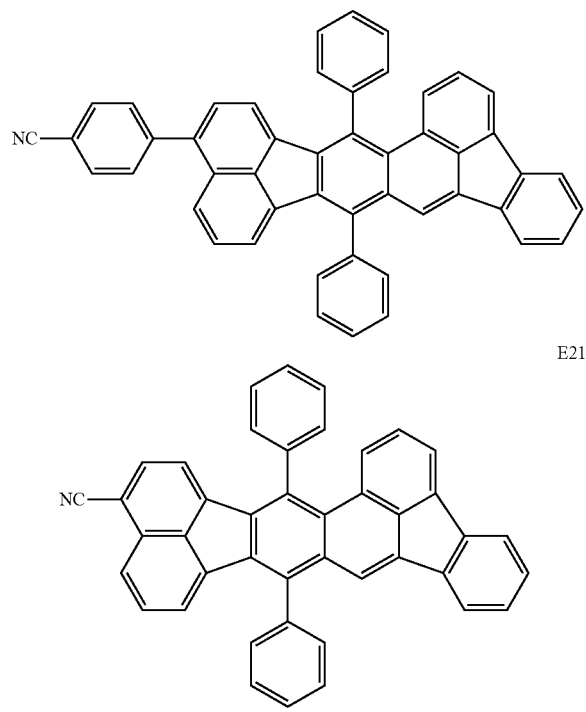

E20

E21

(Other Constituent Material for Organic Light Emitting Element)

In the organic light emitting element of the present invention, in addition to the electron donor-property compound and the electron acceptor-property compound, a known compound can be used as a constituent material to be incorporated into the element. Examples of such compound are given below.

A material having a high hole mobility is preferred as a hole injectable/transportable material so that the injection of a hole from the anode may be facilitated and the injected hole can be transported to the emission layer. In addition, a material having a high glass transition temperature is preferred in order to prevent the deterioration of film quality such as crystallization in the organic light emitting element. A triarylamine derivative, an arylcarbazole derivative, a phenylenediamine derivative, a stilbene derivative, a phthalocyanine derivative, a porphyrin derivative, poly(vinyl carbazole), poly(thiophene), and any other conductive polymer are given as a low-molecular material or high-molecular material having hole injection/transport performance. Further, the hole injectable/transportable material is also suitably used for an electron blocking layer.

Specific examples of the compound to be used as the hole injectable/transportable material are shown below. However, the compound is of course not limited to the following.

HT1

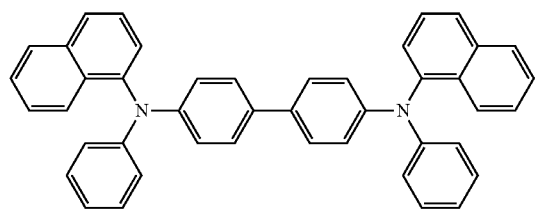

HT2

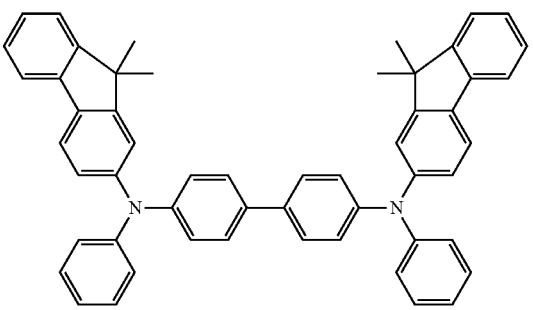

HT3

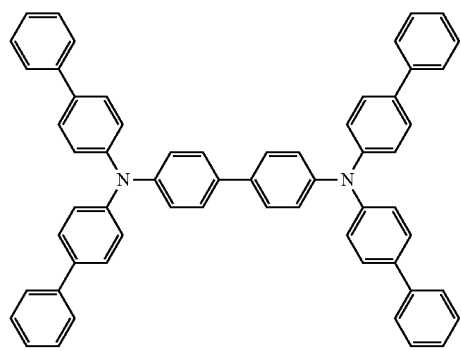

HT4

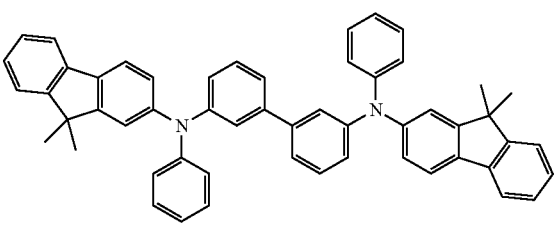

-continued
HT5
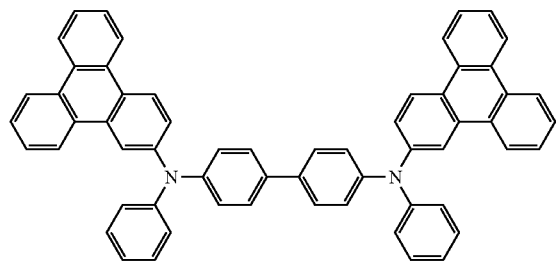
HT6
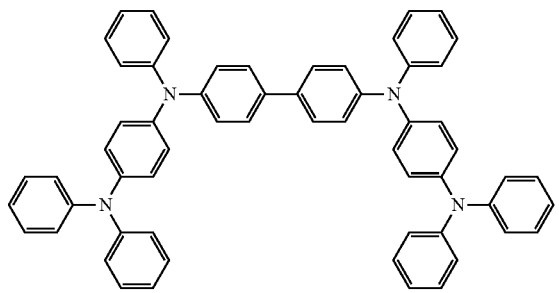
HT7
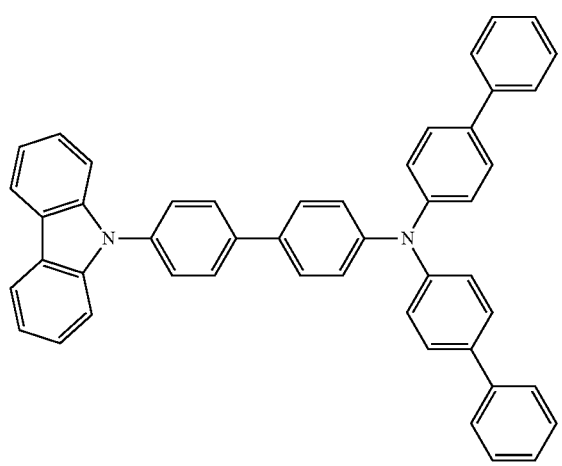
HT8
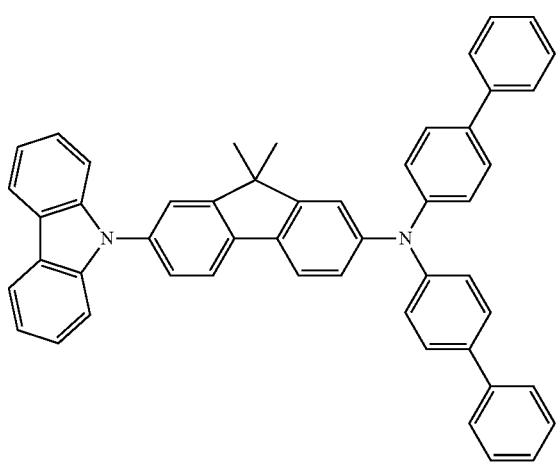
HT9
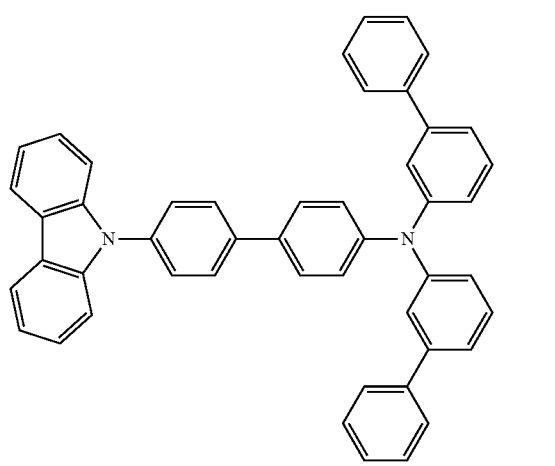
HT10
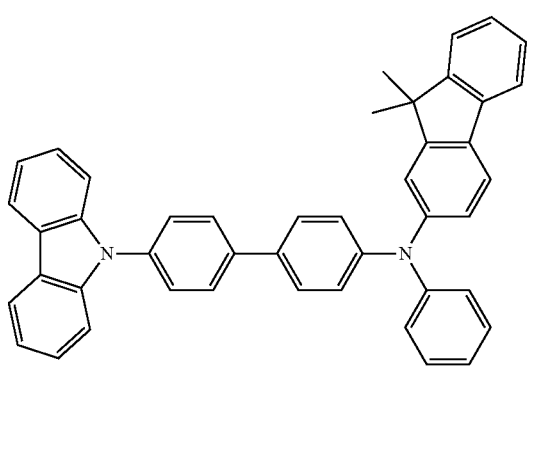
HT11
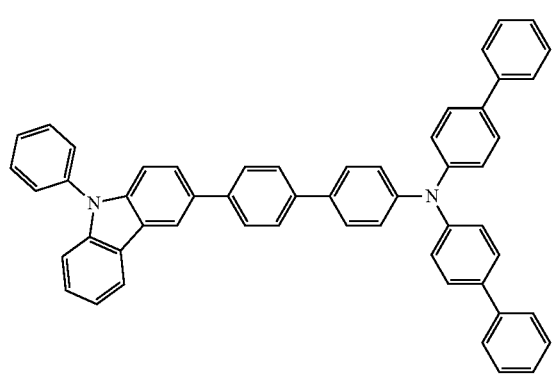
HT12
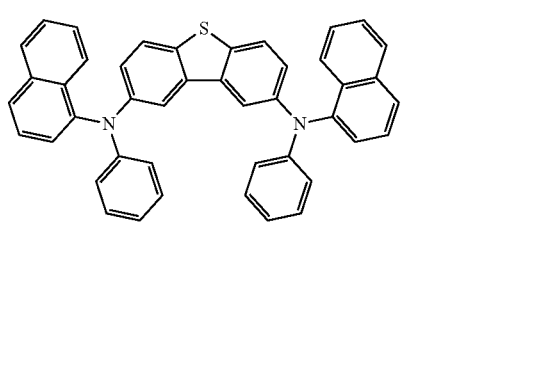

HT13

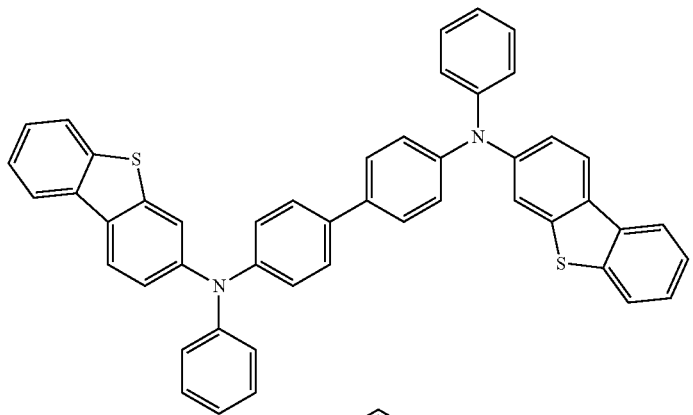

HT14

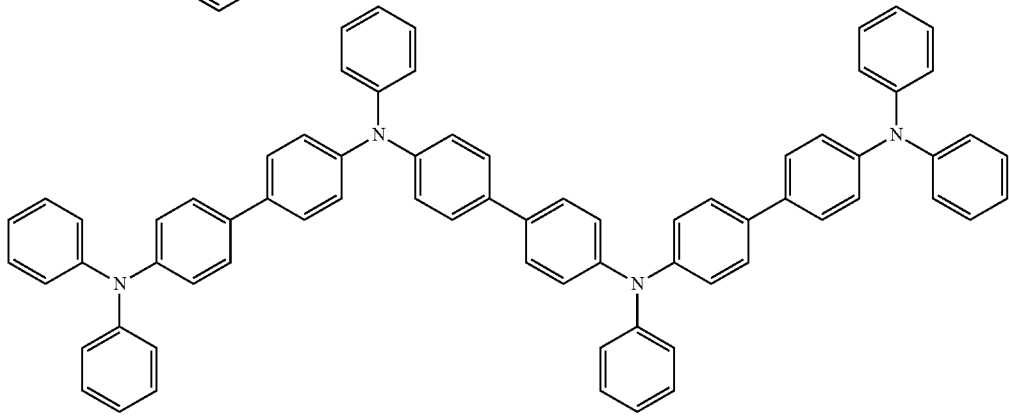

As a light emitting material mainly involved in light emitting function among constituent materials for the emission layer, there are given, for example, condensed ring compounds (such as a fluorene derivative, a naphthalene derivative, a pyrene derivative, a perylene derivative, a tetracene derivative, an anthracene derivative, and rubrene), a quinacridone derivative, a coumarin derivative, a stilbene derivative, an organic aluminum complex such as tris(8-quinolinolato)aluminum, an iridium complex, a platinum complex, a rhenium complex, a copper complex, a europium complex, a ruthenium complex, and polymer derivatives such as a poly(phenylene vinylene) derivative, a poly(fluorene) derivative, and a poly(phenylene) derivative.

Specific examples of the compound to be used as the light emitting material are shown below. However, the compound is of course not limited to the following.

BD1

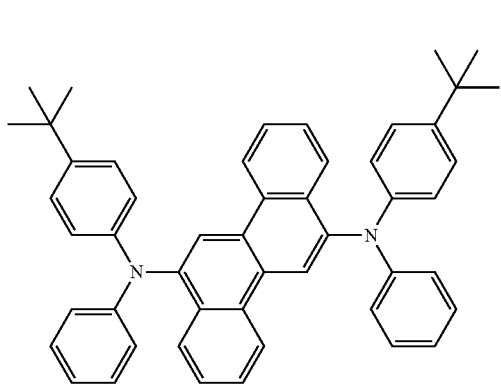

BD2

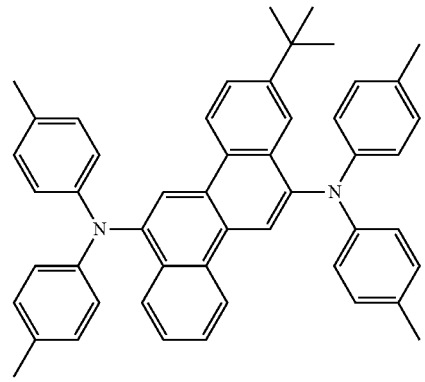

BD3

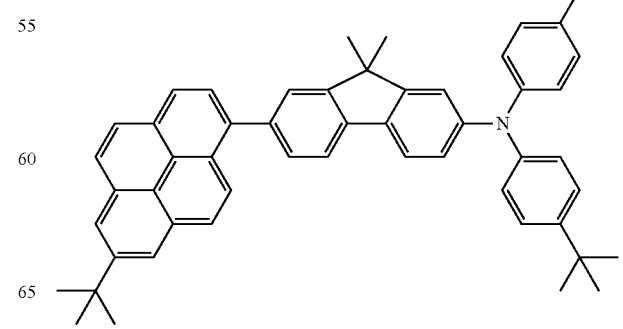

BD4
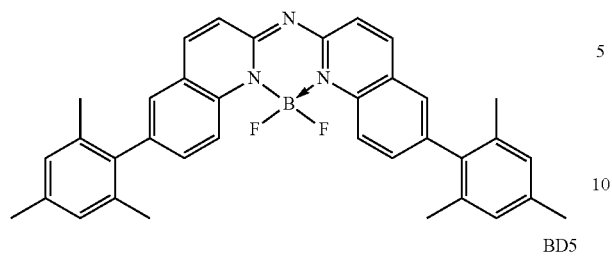
BD5
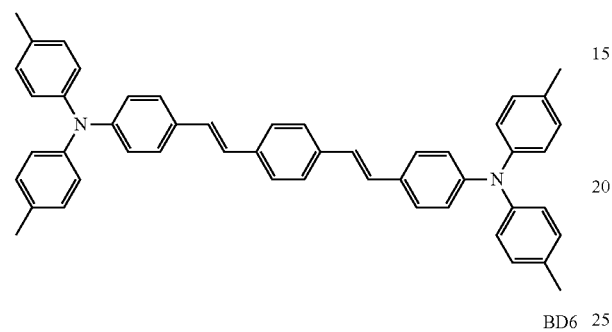
BD6
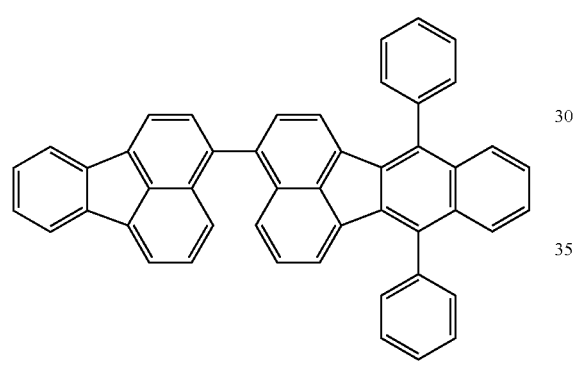
BD7
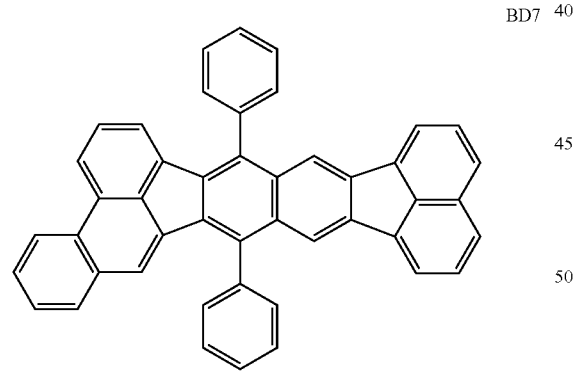
BD8
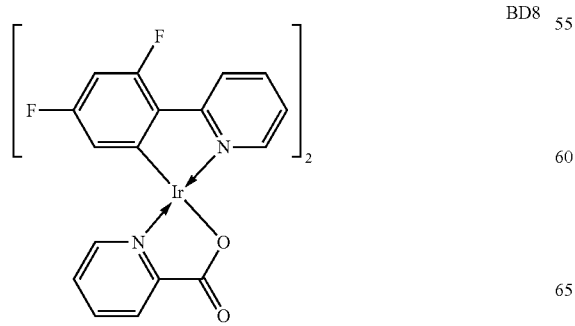
GD1
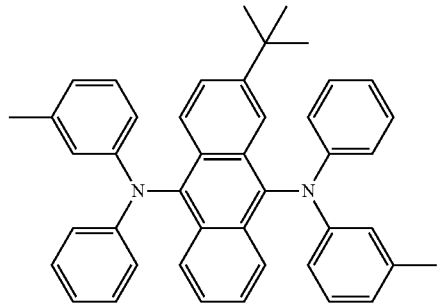
GD2
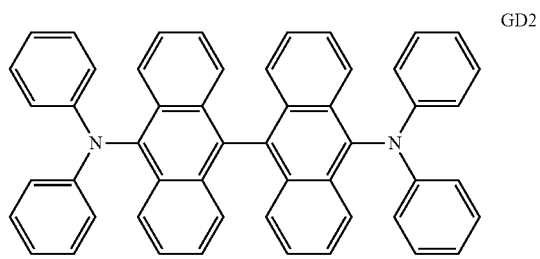
GD3
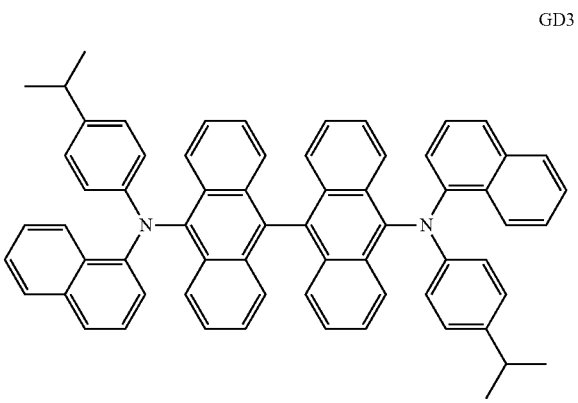
GD4
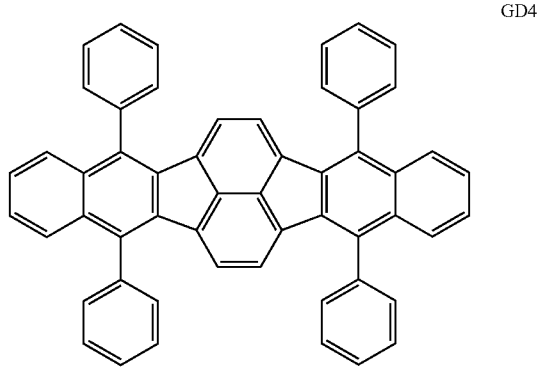

GD5
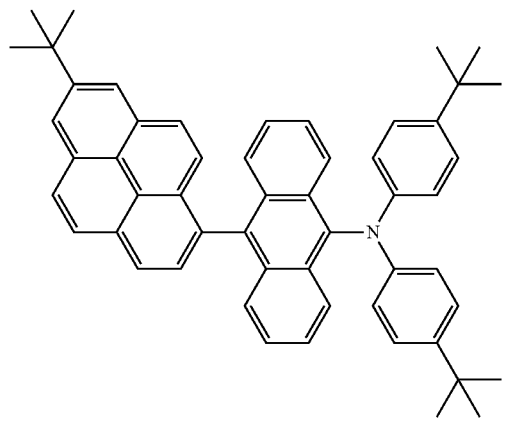
GD6
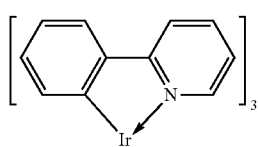
GD7
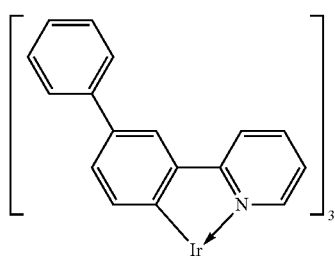
GD8
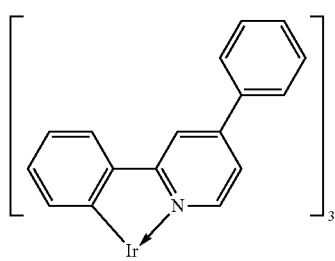
RD1
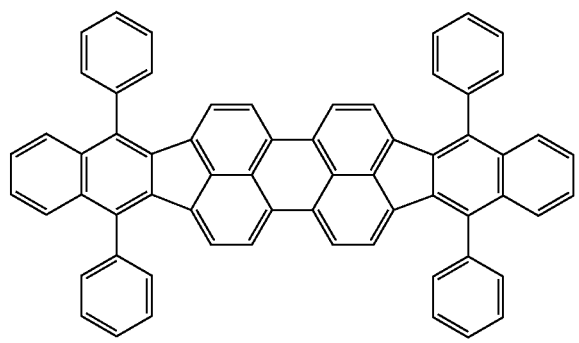
RD2
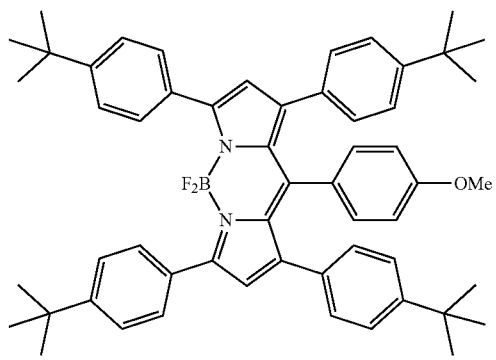
RD3
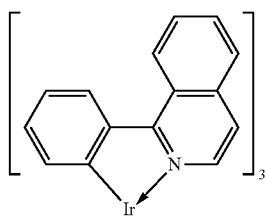
RD4
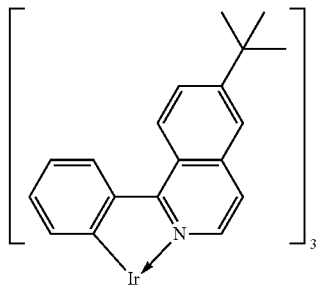
RD5
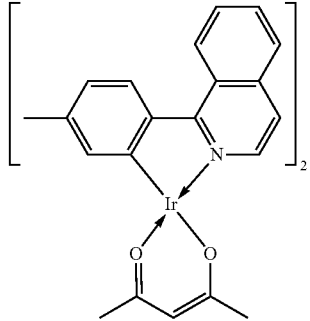

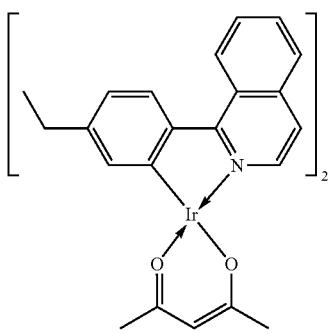

RD6

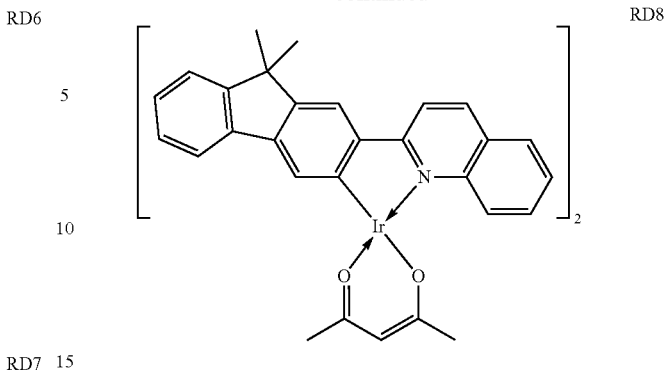

RD8

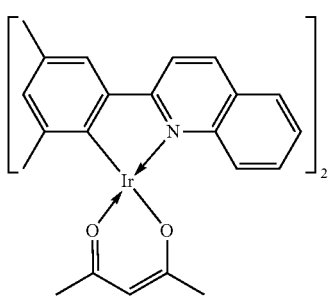

RD7

As a host or an assist material (emission assist material) to be incorporated into the emission layer, there are given, for example, an aromatic hydrocarbon compound and a derivative thereof as well as a carbazole derivative, a dibenzofuran derivative, a dibenzothiophene derivative, an organic aluminum complex such as a tris(8-quinolinolato) aluminum, and an organic beryllium complex.

Specific examples of the compound to be used as the host (emission layer host) or emission assist material to be incorporated into the emission layer are shown below. However, the compound is of course not limited to the following.

EM1

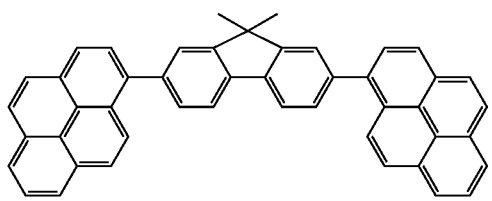

EM2

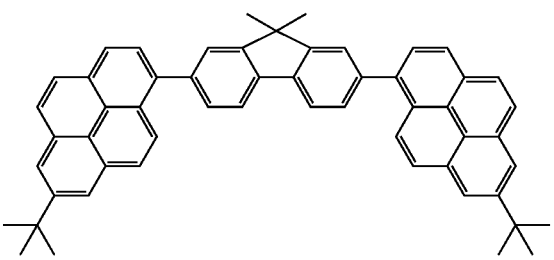

EM3

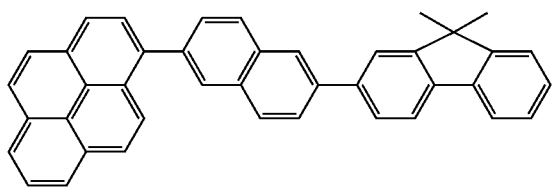

EM4

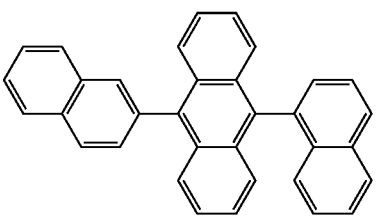

EM5

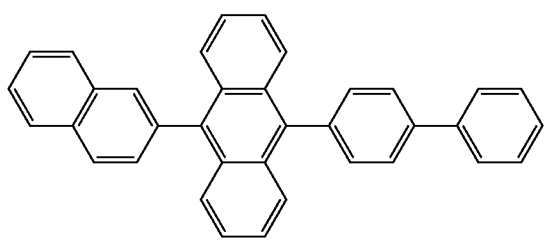

EM6

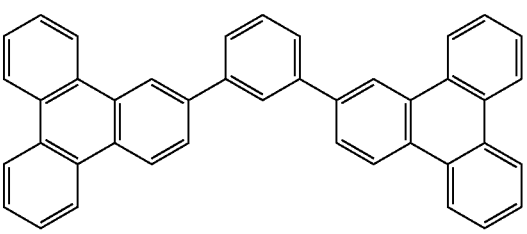

-continued
EM7
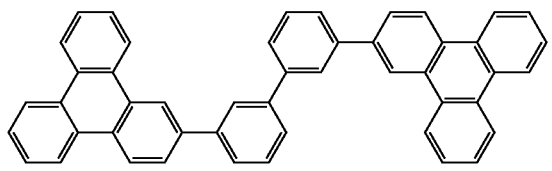
EM8
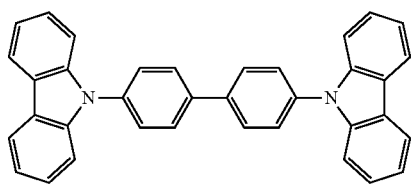
EM9
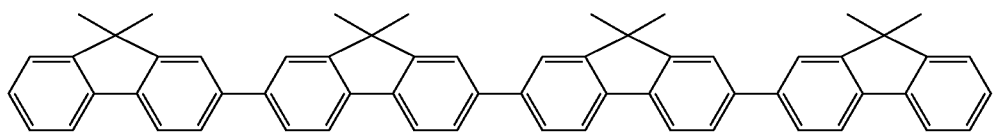
EM10
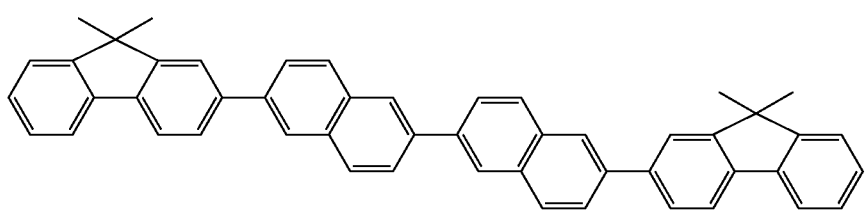
EM11
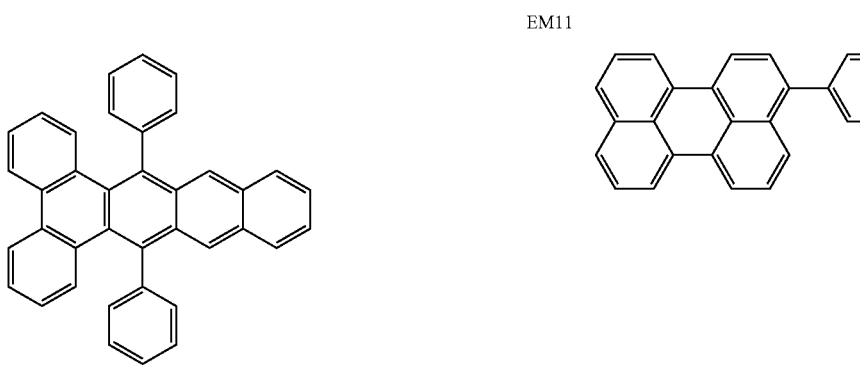
EM12
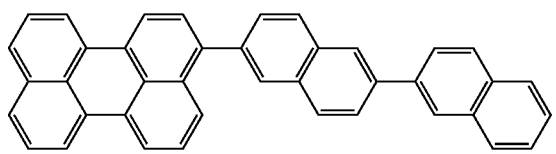
EM13
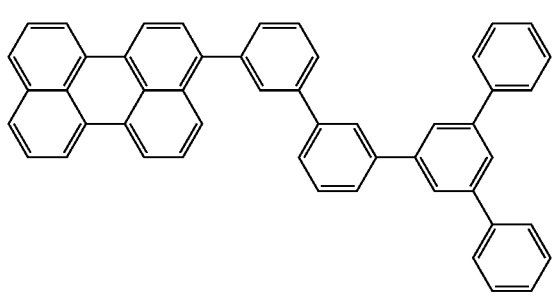
EM14
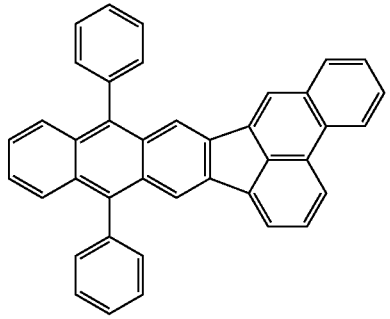
EM15
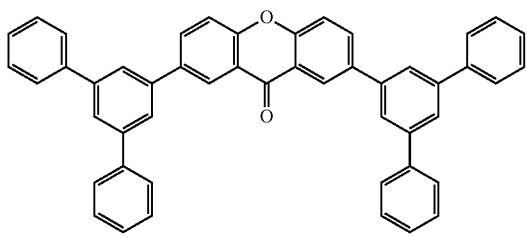
EM16
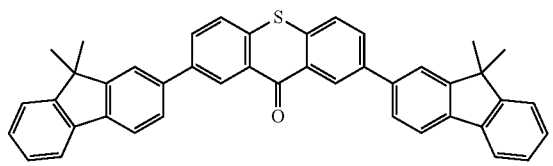

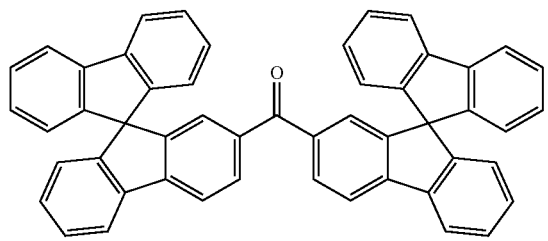

EM17

An electron transportable material can be arbitrarily selected from materials that can transport an electron injected from the cathode to the emission layer, and the material is appropriately selected in consideration of, for example, the balance with the hole mobility of the hole transportable material. Examples of the material having electron transport performance include an oxadiazole derivative, an oxazole derivative, a pyrazine derivative, a triazole derivative, a triazine derivative, a quinoline derivative, a quinoxaline derivative, a phenanthroline derivative, an organic aluminum complex, and condensed ring compounds (such as a fluorene derivative, a naphthalene derivative, a chrysene derivative, and an anthracene derivative). Further, the electron transportable material is also suitably used for the hole blocking layer.

Specific examples of the compound to be used as the electron transportable material are shown below. However, the compound is of course not limited to the following.

ET1

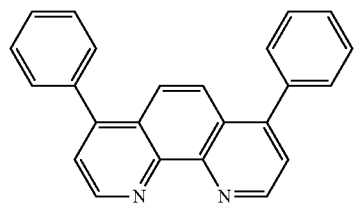

ET4

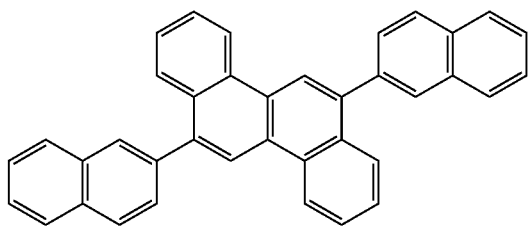

ET5

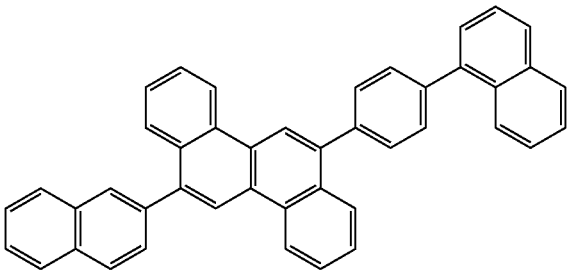

ET2

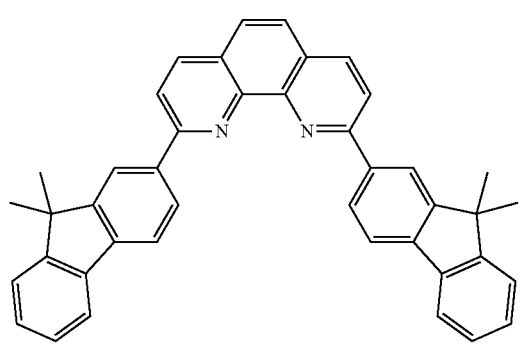

ET6

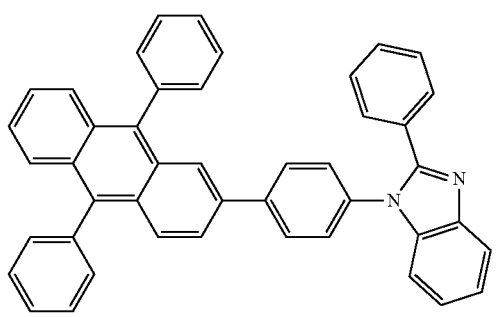

ET3

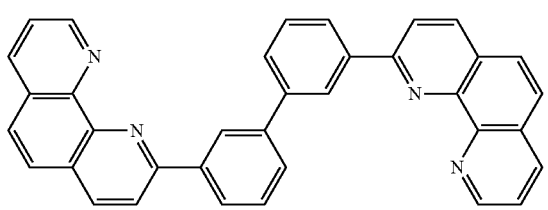

ET7

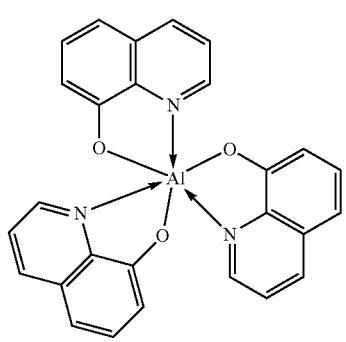

ET8

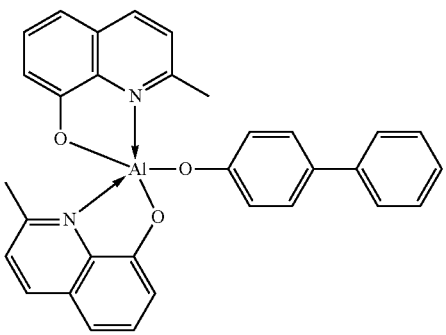

ET9

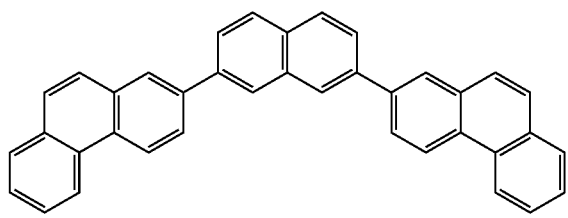

ET10

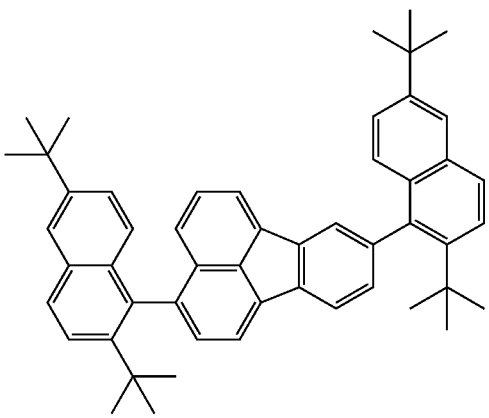

An electron injectable material can be arbitrarily selected from materials that can facilitate the injection of an electron from the cathode, and the material is selected in consideration of, for example, balance with a hole injection property. The electron injectable material includes the electron donor-property compound (viologen compound) that has already been described, an n-type dopant, and a reducing dopant as well. In addition to the viologen compound to be incorporated into the organic light emitting element of the present invention, examples of such material having electron injection performance include an alkali metal, an alkaline earth metal, a rare earth metal, an oxide of an alkali metal, a halide of an alkali metal, a carbonate of an alkali metal, an alkali metal complex, an oxide of an alkaline earth metal, a halide of an alkaline earth metal, an alkaline earth metal complex, an oxide of a rare earth metal, a halide of a rare earth metal, and a rare earth metal complex.

A constituent material for the anode desirably has as large a work function as possible. Examples thereof may include: metal simple substances such as gold, platinum, silver, copper, nickel, palladium, cobalt, selenium, vanadium, and tungsten or alloys obtained by combining these metal simple substances; metal oxides such as tin oxide, zinc oxide, indium oxide, indium tin oxide (ITO), and indium zinc oxide; and conductive polymers such as polyaniline, polypyrrole, and polythiophene.

One kind of those electrode substances may be used alone, or two or more kinds thereof may be used in combination. In addition, the anode may have a single-layer construction or may have a multilayer construction.

On the other hand, a constituent material for the cathode is desirably one having as small a work function as possible, but is not limited thereto. Examples thereof include: alkali metals such as lithium; alkaline earth metals such as calcium; and metal simple substances such as aluminum, titanium, manganese, silver, lead, chromium, and gold.

Alternatively, alloys obtained by combining those metal simple substances can be used. For example, a magnesium-silver alloy, an aluminum-lithium alloy, or an aluminum-magnesium alloy can be used. A metal oxide such as indium tin oxide (ITO) can also be utilized. One kind of those electrode substances may be used alone, or two or more kinds thereof may be used in combination. In addition, the cathode may have a single-layer construction or may have a multilayer construction.

In the organic light emitting element of the present invention, a light extraction construction may be a bottom emission construction (construction in which light is extracted from a substrate side) or may be a top emission construction (construction in which light is extracted from a side opposite to the substrate). In the case of the bottom emission construction, while a first electrode to be formed on the substrate side is an optically transparent electrode or semitransparent electrode, a second electrode to be formed on the side opposite to the substrate is a light reflective electrode. In addition, in the case of the top emission construction, while the first electrode is the light reflective electrode, the second electrode is the optically transparent electrode or semitransparent electrode. A metal conductive layer having a large thickness (of 80 nm or more and 600 nm or less) can be used as the light reflective electrode. In addition, a metal conductive layer having a small thickness (of from 15 nm to 35 nm) can be used as the semitransparent electrode.

The organic light emitting element of the present invention is preferably sealed in order to suppress the contact of oxygen, moisture, or the like. A method of sealing the organic light emitting element of the present invention is, for example, a method involving forming a sealing layer on the organic light emitting element, specifically on the second electrode. Examples of a constituent material for the sealing layer for sealing the organic light emitting element include materials such as: inorganic oxides, inorganic nitrides, and inorganic oxynitrides such as $SiO_2$, SiN, and SiON; polymer compounds such as a fluorine resin, polyparaxylene, polyethylene, a silicone resin, and a polystyrene resin; and photocurable resins. In addition, a member formed by an atomic layer deposition (ALD) method on the second electrode can be used as the sealing layer.

In addition, an organic film layer such as an optical interference layer can be formed on the second electrode.

The organic compound layer (such as the hole injection layer, the hole transport layer, the electron blocking layer, the emission layer, the hole blocking layer, the electron transport layer, or the electron injection layer) for forming the organic light emitting element of the present invention is formed by the following method.

A dry process such as a vacuum vapor deposition method, an ionized vapor deposition method, sputtering, or a plasma process can be used for the formation of the organic compound layer for forming the organic light emitting element of the present invention. In addition, a wet process involving dissolving the constituent materials in an appropriate solvent and forming a layer by a known application method (such as spin coating, dipping, a casting method, an LB method, or an ink jet method) can be used instead of the dry process.

Here, when the layer is formed by the vacuum vapor deposition method, or the solution application method the layer hardly undergoes crystallization and is excellent in stability over time. In addition, when the layer is formed by the application method, the film can be formed by using the constituent materials in combination with an appropriate binder resin.

Examples of the binder resin include, but not limited to, a polyvinyl carbazole resin, a polycarbonate resin, a polyester resin, an ABS resin, an acrylic resin, a polyimide resin, a phenol resin, an epoxy resin, a silicone resin, and a urea resin.

In addition, one kind of those binder resins may be used alone as a homopolymer or a copolymer, or two or more kinds thereof may be used as a mixture. Further, a known additive such as a plasticizer, an antioxidant, or a UV absorber may be used in combination as required.

(Application of Organic Light Emitting Element)

The organic light emitting element of the present invention can be used as a constituent member for a display device or lighting device. In addition, the element finds use in applications such as an exposure light source for an image forming device of an electrophotographic system, a backlight for a liquid crystal display device, and a light emitting device including a white light source and a color filter. Examples of the color filter include filters that transmit light beams having three colors, i.e., red, green, and blue colors.

A display device of the present invention includes the organic light emitting element of the present invention in its display portion. It should be noted that the display portion includes a plurality of pixels.

In addition, the pixels each include the organic light emitting element of the present invention and a transistor as an example of an active element (switching element) or amplifying element configured to control emission luminance, and the anode or cathode of the organic light emitting element and the drain electrode or source electrode of the transistor are electrically connected to each other. Here, the display device can be used as an image display device for a PC or the like. The transistor is, for example, a TFT element and the TFT element is provided on, for example, the insulating surface of a substrate. In addition, the TFT element preferably includes an electrode formed of a transparent oxide semiconductor.

The display device may be an image information processing device that includes an image input portion configured to input image information from, for example, an area CCD, a linear CCD, or a memory card, and displays an input image on its display portion.

In addition, the display portion of an imaging device or inkjet printer may have a touch panel function. The drive system of the touch panel function is not particularly limited.

In addition, the display device may be used in the display portion of a multifunction printer.

A lighting device is a device configured to light, for example, the inside of a room. The lighting device may emit light having any one of the following colors: a white color (having a color temperature of 4,200 K), a daylight color (having a color temperature of 5,000 K), and colors ranging from blue to red colors.

A lighting device of the present invention includes the organic light emitting element of the present invention and an AC/DC converter circuit (circuit configured to convert an AC voltage into a DC voltage) connected to the organic light emitting element and configured to supply a driving voltage to the organic light emitting element. It should be noted that the lighting device may further include a color filter.

An image forming device of the present invention is an image forming device including: a photosensitive member; a charging unit configured to charge the surface of the photosensitive member; an exposing unit configured to expose the photosensitive member to form an electrostatic latent image; and a developing device configured to develop the electrostatic latent image formed on the surface of the photosensitive member. Here, the exposing unit such as an exposing device to be provided in the image forming device includes the organic light emitting element of the present invention.

In addition, the organic light emitting element of the present invention can be used as a constituent member (light emitting member) for an exposing device configured to expose a photosensitive member. An exposing device including a plurality of the organic light emitting elements of the present invention is, for example, an exposing device in which the organic light emitting elements of the present invention are placed to form a line along a predetermined direction.

Next, the display device of the present invention is described with reference to the drawings. FIG. 1 is a schematic sectional view illustrating an example of a display device including an organic light emitting element and a switching element (TFT element) connected to the organic light emitting element. It should be noted that the organic light emitting element of the present invention is used as the organic light emitting element constituting a display device 1 of FIG. 1.

The display device 1 of FIG. 1 includes a substrate 11 made of glass and a moisture-proof film 12 for protecting a TFT element 18, which serves as a switching element, or organic compound layer, the film being formed on the substrate. In addition, the display device 1 of FIG. 1 includes a metal gate electrode 13, a gate insulating film 14, and a semiconductor layer 15.

A TFT element 18 includes the semiconductor layer 15, a drain electrode 16, and a source electrode 17. An insulating film 19 is formed on the TFT element 18. An anode 21 constituting the organic light emitting element and the source electrode 17 are connected to each other through a contact hole 20.

It should be noted that a system for the electrical connection between the electrode (anode or cathode) in the organic light emitting element and the electrode (source electrode or drain electrode) in the TFT is not limited to the aspect illustrated in FIG. 1. In other words, one of the anode and the cathode, and one of the source electrode and drain electrode of the TFT element only need to be electrically connected to each other.

Although a plurality of organic compound layers are illustrated like one layer in the display device 1 of FIG. 1, an organic compound layer 22 may be a plurality of layers. A first protective layer 24 and second protective layer 25 for suppressing the deterioration of the organic light emitting element are formed on a cathode 23.

When the display device 1 of FIG. 1 is a display device that emits white light, an emission layer in the organic compound layer 22 in FIG. 1 may be a layer obtained by mixing a red light emitting material, a green light emitting material, and a blue light emitting material. In addition, the layer may be a laminated emission layer obtained by laminating a layer formed of the red light emitting material, a layer formed of the green light emitting material, and a layer formed of the blue light emitting material. Further, alternatively, the following aspect is permitted: the layer formed of the red light emitting material, the layer formed of the green light emitting material, and the layer formed of the blue light emitting material are, for example, arranged side by side to form domains in one emission layer.

Although the transistor is used as the switching element in the display device 1 of FIG. 1, an MIM element may be used instead of the transistor as the switching element.

In addition, the transistor to be used in the display device 1 of FIG. 1 is not limited to a transistor using a monocrystalline silicon wafer and may be a thin-film transistor including an active layer on the insulating surface of a substrate. In addition, a thin-film transistor using monocrystalline silicon as the active layer, a thin-film transistor using non-monocrystalline silicon such as amorphous silicon or microcrystalline silicon as the active layer, a thin-film transistor using a non-monocrystalline oxide semiconductor such as indium zinc oxide or indium gallium zinc oxide as the active layer, an organic transistor using a film formed of an organic material as the active layer can also be used. It should be noted that the thin-film transistor is also called a TFT element.

The channel portion of the switching element according to this embodiment may contain an oxide semiconductor.

In the switching element, an oxide semiconductor portion may be in an amorphous state, a crystalline state, or such a state that both the states are mixed. The crystal may be any one of a single crystal, a microcrystal, and a crystal whose specific axis such as a C-axis is oriented, or a mixture of at least two kinds thereof.

The organic light emitting element including such switching element may be used in an image display device in which each organic light emitting element is provided as a pixel, or may be used as a lighting device or as an exposure portion for exposing a photosensitive member of an image forming device of an electrophotographic system such as a laser beam printer or a copying machine.

The transistor in the display device 1 of FIG. 1 may be formed in a substrate such as a Si substrate. Here, the phrase "formed in a substrate" means that the transistor is produced by processing the substrate itself such as a Si substrate. In other words, the presence of the transistor in the substrate can be regarded as follows: the substrate and the transistor are integrally formed.

Whether the transistor is provided in the substrate is selected depending on definition. In the case of, for example, a definition of about a QVGA per inch, the organic light emitting element is preferably provided in the Si substrate.

As described above, the driving of the display device using the organic light emitting element of the present invention enables display that has good image quality and is stable over a long time period.

Figure 2:
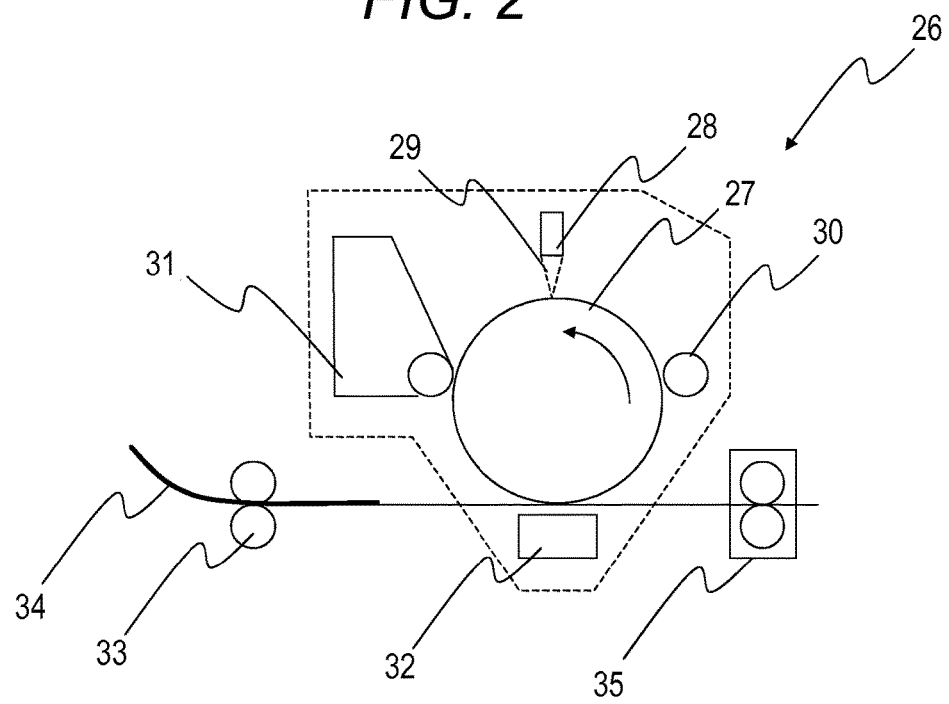
FIG. 2 is a schematic view illustrating an example of an image forming device including the organic light emitting element according to the present invention.

Next, other applications of the organic light emitting element of the present invention are described. FIG. 2 is a schematic view illustrating an example of an image forming device including the organic light emitting element according to the present invention. An image forming device 26 of FIG. 2 includes a photosensitive member 27, an exposure light source 28, a developing device 30, a charging portion 31, a transferring device 32, a conveying roller 33, and a fixing device 35.

In the image forming device 26 of FIG. 2, light 29 is applied from the exposure light source 28 to the photosensitive member 27, whereby an electrostatic latent image is formed on the surface of the photosensitive member 27. In the image forming device 26 of FIG. 2, the exposure light source 28 includes the organic light emitting element according to the present invention. In addition, in the image forming device 26 of FIG. 2, the developing device 30 as a developing portion has a developer such as toner and is configured to apply the developer to the photosensitive member 27. In the image forming device 26 of FIG. 2, the charging portion 31 is provided for charging the photosensitive member 27. In the image forming device 26 of FIG. 2, the transferring device 32 is provided for transferring a developed image onto a recording medium 34 such as paper. It should be noted that the recording medium 34 is conveyed by the conveying roller 33 to the transferring device 32. In the image forming device 26 of FIG. 2, the fixing device 35 is provided for fixing the image formed on the recording medium 34.

Figure 3A:
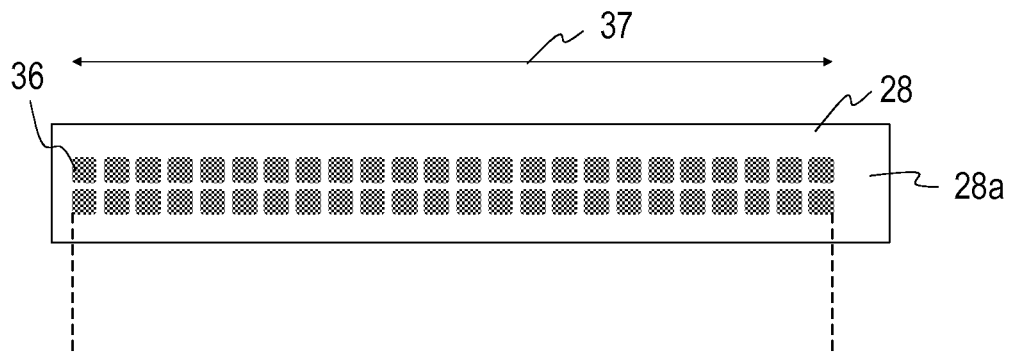
FIG. 3A is a schematic plan view illustrating a specific example of a member constituting the image forming device of FIG. 2.
Figure 3B:
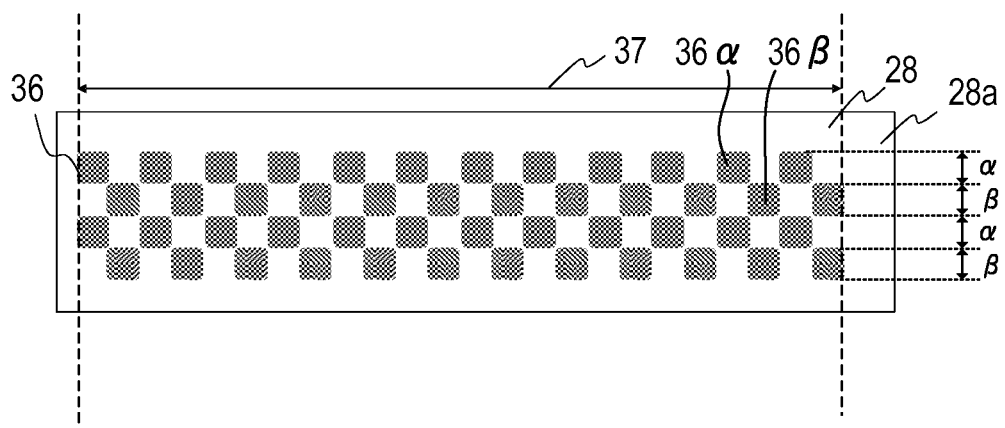
FIG. 3B is a schematic plan view illustrating a specific example of an exposure light source constituting the image forming device of FIG. 2.
Figure 3C:
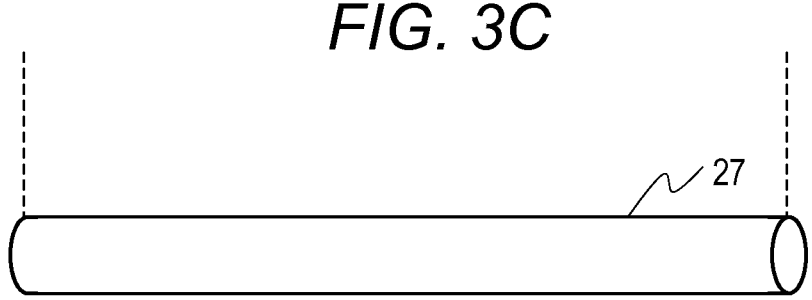
FIG. 3C is a schematic view illustrating a specific example of a photosensitive member constituting the image forming device of FIG. 2.

FIG. 3A and FIG. 3B are each a schematic plan view illustrating a specific example of the exposure light source constituting the image forming device 26 of FIG. 2, and FIG. 3C is a schematic view illustrating a specific example of the photosensitive member constituting the image forming device 26 of FIG. 2. It should be noted that FIG. 3A and FIG. 3B have the following feature in common: a plurality of emission portions 36 (emission points) each including the organic light emitting element are placed on an elongated substrate 28a of the exposure light source 28. In addition, an arrow represented by reference numeral 37 represents a column direction in which the emission portions 36 are arranged. The column direction is the same as the direction of the axis about which the photosensitive member 27 rotates.

By the way, FIG. 3A illustrates a form in which the plurality of emission portions 36 of the exposure light source 28 are placed along the long axis direction of the photosensitive member 27. On the other hand, FIG. 3B illustrates a form in which the emission portions 36 are alternately placed in the column direction in a first column α and a second column β. In FIG. 3B, the first column α and the second column β are placed at different positions in a row direction.

In addition, in FIG. 3B, while a plurality of emission portions 36α are placed at a certain interval in the first column α, the second column β has an emission portion 36β at a position corresponding to an interval between the emission portions 36α in the first column α. That is, in the exposure light source of FIG. 3B, the plurality of emission portions are placed at a certain interval in the row direction as well.

It should be noted that the following rewording is permitted: the exposure light source of FIG. 3B is in a state in which the emission portions (36α and 36β) constituting the exposure light source are placed in, for example, a lattice, hound's-tooth, or checkered pattern.

Figure 4:
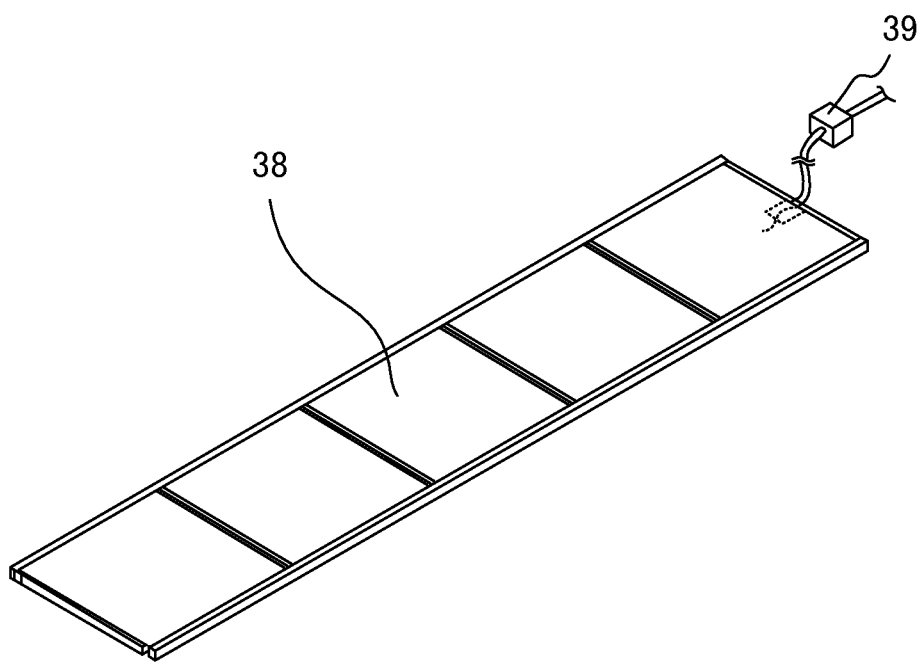
FIG. 4 is a schematic view illustrating an example of a lighting device including the organic light emitting element according to the present invention.

FIG. 4 is a schematic view illustrating an example of a lighting device including the organic light emitting element according to the present invention. The lighting device of FIG. 4 includes an organic light emitting element 38 provided on a substrate (not shown) and an AC/DC converter circuit 39. In addition, the lighting device of FIG. 4 may include a heat sink (not shown) corresponding to a heat discharging portion for discharging heat in the device to the outside on, for example, a substrate surface on a side opposite to the side on which the organic light emitting element 38 is mounted.

EXAMPLES

Now, the present invention is described by way of Examples. However, the present invention is not limited to Examples described below.

(Electron Donor-Property Compound X (Viologen Compound))

The viologen compound as the electron donor-property compound X used in the production of the organic light emitting element of the present invention was synthesized by an existing method. Specifically, as represented by the following reaction formula, the viologen compound was obtained by reducing a halide salt as a precursor of the compound.

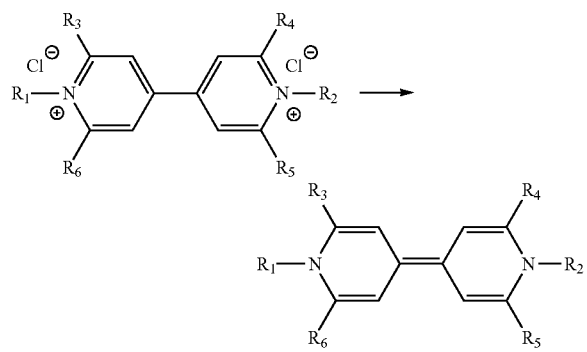

As a method of reducing the halide salt, there is known, for example, (i) a reduction method involving using zinc or (ii) a reduction method involving using a hyposulfite ion. Here, the methods (i) and (ii) are described by taking the synthesis of Exemplified Compound C1 as a specific example. It should be noted that the synthesis scheme of Exemplified Compound C1 is as shown below.

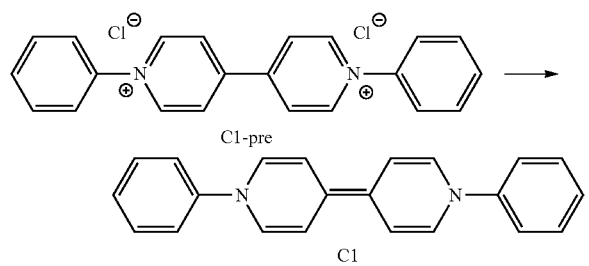

<Reduction Method Involving Using Zinc (Method (i))>

Compound C1-pre, zinc powder, and ethanol were loaded into a reaction vessel, and then the reaction solution was heated to reflux for 8 hours. Thus, Exemplified Compound C1 was obtained.

<Reduction Method Involving Using Hyposulfite Ion (Method (ii))>

Compound C1-pre, 10% ammonia water, sodium hyposulfite, and ethanol were loaded into a reaction vessel, and then the reaction solution was stirred at room temperature for 1 hour. Thus, Exemplified Compound C1 was obtained.

(CV Measurement)

A halide salt as a precursor of the electron donor-property compound X and the electron acceptor-property compound Y were subjected to CV measurement. Specific measurement conditions are listed below.

Measurement environment (gas atmosphere): nitrogen atmosphere
Electrolytic solution: 0.1 M tetrabutylammonium perchlorate solution in DMF
Reference electrode: Ag/Ag$^+$
Counter electrode: Pt
Working electrode: glassy carbon
Measurement device: electrochemical analyzer (manufactured by ALS, model 660C)
Sweeping rate: 1.0 V/s Table 2 shows the first reduction potential value ($V_{red}$) of the electron acceptor-property compound Y and the first oxidation potential value ($V_{ox}$) of the electron donor-property compound X obtained under the measurement conditions. It should be noted that in each of the $V_{red}$ and the $V_{ox}$, in consideration of a measurement error, when the second decimal place of a measured value was 0, 1, 2, 8, or 9, the second decimal place was set to 0, and when the second decimal place of the measured value was 3, 4, 5, 6, or 7, the second decimal place was set to 5.

Example 1

In this example, an organic light emitting element of a bottom emission construction in which an anode, a hole transport layer, an electron blocking layer, an emission layer, an electron transport layer, an electron injection layer, and a cathode were formed in the stated order on a substrate was produced by a method to be described below.

Indium tin oxide (ITO) was formed into a film on a glass substrate by a sputtering method. Thus, the anode was formed. At this time, the thickness of the anode was set to 120 nm. Next, the substrate having formed thereon the anode was sequentially subjected to ultrasonic washing with acetone and isopropyl alcohol (IPA), and was then subjected to boil washing with IPA, followed by drying. Further, the dried product was subjected to UV/ozone washing. The substrate treated by the foregoing method was used as a transparent conductive supporting substrate (ITO substrate) in the next step.

Next, layers and an electrode layer shown in Table 1 below were continuously formed on the ITO substrate by vacuum deposition based on resistance heating in a vacuum chamber at $10^{-5}$ Pa. At this time, the layers were formed so that an opposing electrode area became 3 mm$^2$.

TABLE 1

| | Constituent material | Thickness [nm] |
| --- | --- | --- |
| Hole transport layer | HT2 | 50 |
| Electron blocking layer | HT7 | 10 |
| Emission layer | Host: EM12<br>Guest: RD1<br>(Host:guest = 99.5:0.5 (weight ratio)) | 30 |
| Electron transport layer | ET6 | 50 |
| Electron injection layer | C1 (Electron donor-property compound), E10 (Electron acceptor-property compound)<br>(C1:E10 = 40:60 (weight ratio)) | 15 |
| Metal electrode layer (cathode) | Al | 100 |

The resultant organic light emitting element was driven so that its luminance became 100 cd/m$^2$. As a result, its light emitting efficiency was 0.9 cd/A and red light emission was observed.

Examples 2 to 12

Organic light emitting elements were each produced by the same method as that of Example 1 except that in Example 1, the constituent materials for the electron injection layer were changed as shown in Table 2 below. The resultant organic light emitting elements were evaluated for their element characteristics by the same method as that of Example 1. Table 2 shows the results.

Comparative Example 1

An organic light emitting element was produced by the same method as that of Example 1 except that in Example 1, only Compound C1 was formed into a film having a thickness of 0.5 Å in the formation of the electron injection layer. The resultant organic light emitting element was evaluated for its element characteristic by the same method as that of Example 1. Table 2 shows the result.

TABLE 2

| | Electron injection layer | | | | |
|---|---|---|---|---|---|
| | Donor | | Acceptor | | |
| | | $V_{ox}$ (V) | | $V_{red}$ (V) | $V_{ox} - V_{red}$ (V) | Efficiency (cd/A) |
| Example 1 | C1 | −0.90 | E12 | −0.90 | 0 | 0.9 |
| Example 2 | C1 | −0.90 | E9 | −1.80 | 0.90 | 0.5 |
| Example 3 | C1 | −0.90 | E5 | −2.30 | 1.40 | 0.1 |
| Example 4 | C2 | −0.95 | E12 | −0.90 | −0.05 | 1.3 |
| Example 5 | C2 | −0.95 | E9 | −1.80 | 0.85 | 0.6 |
| Example 6 | C3 | −1.05 | E9 | −1.80 | 0.75 | 1.5 |
| Example 7 | C13 | −1.05 | E9 | −1.80 | 0.75 | 1.5 |
| Example 8 | C15 | −1.00 | E9 | −1.80 | 0.80 | 1.2 |
| Example 9 | C16 | −1.00 | E9 | −1.80 | 0.80 | 0.8 |
| Example 10 | B1 | −1.20 | E12 | −0.90 | −0.30 | 1.4 |
| Example 11 | B1 | −1.20 | E9 | −1.80 | 0.60 | 1.0 |
| Example 12 | B4 | −0.10 | E10 | −0.10 | 0 | 0.3 |
| Comparative Example 1 | C1 | −0.90 | | | | No light emission |

Examples 13 to 16

Organic light emitting elements were each produced by the same method as that of Example 3 except that in Example 3, the constituent materials for the emission layer were changed as shown in Table 3 below. The resultant organic light emitting elements were evaluated for their element characteristics by the same method as that of Example 3. Table 3 shows the results.

TABLE 3

| | Emission layer | | | | |
|---|---|---|---|---|---|
| | Host | Weight ratio | Dopant | Weight ratio | Efficiency (cd/A) | Luminescent color |
| Example 13 | EM3 | 95% | BD6 | 5% | 0.3 | Blue light emission |
| Example 14 | EM2 | 98% | GD4 | 2% | 1.5 | Green light emission |
| Example 15 | EM10 | 96% | RD3 | 4% | 2.4 | Red light emission |
| Example 16 | EM7 | 90% | GD6 | 10% | 3.5 | Green light emission |

Examples 17 to 31

Organic light emitting elements were each produced by the same method as that of Example 1 except that in Example 1, the constituent materials for the electron injection layer were changed as shown in Table 4 below. The resultant organic light emitting elements were evaluated for their element characteristics by the same method as that of Example 1. Table 4 shows the results.

TABLE 4

| | Electron injection layer | | | | |
|---|---|---|---|---|---|
| | Donor | | Acceptor | | |
| | | $X_{ox}$ (V) | | $Y_{red}$ (V) | $V_{ox} - V_{red}$ (V) | Efficiency (cd/A) |
| Example 17 | C3 | −1.05 | E8 | −1.95 | 0.90 | 1.1 |
| Example 18 | C3 | −1.05 | E19 | −1.85 | 0.80 | 1.6 |
| Example 19 | C3 | −1.05 | E20 | −1.80 | 0.75 | 1.5 |
| Example 20 | C12 | −0.95 | E8 | −1.95 | 1.00 | 0.9 |
| Example 21 | C12 | −0.95 | E9 | −1.80 | 0.85 | 1.3 |
| Example 22 | C12 | −0.95 | E19 | −1.85 | 0.90 | 1.5 |
| Example 23 | C12 | −0.95 | E20 | −1.80 | 0.85 | 1.4 |
| Example 24 | C13 | −1.05 | E19 | −1.85 | 0.80 | 1.5 |
| Example 25 | C19 | −1.00 | E20 | −1.80 | 0.80 | 1.4 |
| Example 26 | C21 | −1.05 | E8 | −1.95 | 0.90 | 1.5 |
| Example 27 | C21 | −1.05 | E19 | −1.85 | 0.80 | 1.6 |
| Example 28 | C22 | −1.05 | E8 | −1.95 | 0.90 | 1.4 |
| Example 29 | C22 | −1.05 | E20 | −1.80 | 0.75 | 1.6 |
| Example 30 | C26 | −1.05 | E8 | −1.95 | 0.90 | 1.3 |
| Example 31 | C26 | −1.05 | E19 | −1.85 | 0.80 | 1.5 |

Example 32

An organic light emitting element of a bottom emission construction as described below in which an anode, a hole transport layer, an electron blocking layer, an emission layer, a hole blocking layer, an electron injection/transport layer, and a cathode were formed in the stated order on a substrate was produced. It should be noted that the electron injection/transport layer constituting the organic light emitting element of this example is a layer that brings together the functions of an electron injection layer and an electron transport layer.

Layers and an electrode layer shown in Table 5 below were continuously formed on the ITO substrate produced in Example 1 by vacuum deposition based on resistance heating in a vacuum chamber at $10^{-5}$ Pa. At this time, the layers were formed so that an opposing electrode area became 3 mm$^2$.

TABLE 5

| | Constituent material | Thickness [nm] |
|---|---|---|
| Hole transport layer | HT2 | 50 |
| Electron blocking layer | HT7 | 10 |
| Emission layer | Host: EM14 | 20 |
| | Guest: RD1 | |
| | (Host:guest: = 99.5:0.5 (volume ratio)) | |
| Hole blocking layer | EM15 | 10 |
| Electron injection/transport layer(Note 1) | E19, C3 | 53 |
| Metal electrode layer (cathode) | Aluminum | 120 |

(Note 1)
The electron injection/transport layer is a laminate in which E19 (50 nm, acceptor layer) and C3 (3 nm, donor layer) are laminated in the stated order.

The resultant organic light emitting element was driven so that its luminance became 100 cd/m$^2$. As a result, its light emitting efficiency was 3.5 cd/A and red light emission was observed.

Examples 33 to 39 and Comparative Example 2

Organic light emitting elements were each produced by the same method as that of Example 32 except that in Example 32, the constituent materials for the electron injection/transport layer were changed as shown in Table 6 below. The resultant organic light emitting elements were evaluated for their element characteristics by the same method as that of Example 32. Table 6 shows the results.

TABLE 6

| | Electron injection/ transport layer | | | |
|---|---|---|---|---|
| | Acceptor layer | Donor layer | $V_{ox} - V_{red}$ | Efficiency |
| | $V_{red}$ (V) | $V_{ox}$ (V) | (V) | (cd/A) |
| Example 32 | E19 | −1.85 | C3 | −1.05 | 0.80 | 3.5 |
| Example 33 | E20 | −1.80 | C3 | −1.05 | 0.75 | 3.3 |
| Example 34 | E19 | −1.85 | C12 | −0.95 | 0.90 | 2.5 |
| Example 35 | E20 | −1.80 | C12 | −0.95 | 0.85 | 2.2 |
| Example 36 | E19 | −1.85 | C19 | −1.00 | 0.85 | 2.9 |
| Example 37 | E20 | −1.80 | C19 | −1.00 | 0.80 | 2.6 |
| Example 38 | E19 | −1.85 | C21 | −1.05 | 0.80 | 3.4 |
| Example 39 | E20 | −1.80 | C21 | −1.05 | 0.75 | 3.3 |
| Comparative Example 2 | E5 | −2.30 | | | | No light emission |

Example 40

In this example, an organic light emitting element was produced by the same method as that of Example 1 except that in Example 32, the constituent material for the metal electrode layer (cathode) was changed to silver.

The resultant organic light emitting element was driven so that its luminance became 100 cd/m². As a result, its light emitting efficiency was 4.2 cd/A and red light emission was observed.

Examples 41 to 47

Organic light emitting elements were each produced by the same method as that of Example 40 except that in Example 40, the constituent materials for the electron injection/transport layer were changed as shown in Table 7 below. The resultant organic light emitting elements were evaluated for their element characteristics by the same method as that of Example 40. Table 7 shows the results.

TABLE 7

| | Electron injection/ transport layer | | | |
|---|---|---|---|---|
| | Acceptor layer | Donor layer | $V_{ox} - V_{red}$ | Efficiency |
| | $V_{red}$ (V) | $V_{ox}$ (V) | (V) | (cd/A) |
| Example 40 | E19 | −1.85 | C3 | −1.05 | 0.80 | 4.2 |
| Example 41 | E20 | −1.80 | C3 | −1.05 | 0.75 | 4.0 |
| Example 42 | E19 | −1.85 | C12 | −0.95 | 0.90 | 3.0 |
| Example 43 | E20 | −1.80 | C12 | −0.95 | 0.85 | 2.8 |
| Example 44 | E19 | −1.85 | C19 | −1.00 | 0.85 | 3.5 |
| Example 45 | E20 | −1.80 | C19 | −1.00 | 0.80 | 3.4 |
| Example 46 | E19 | −1.85 | C21 | −1.05 | 0.80 | 4.1 |
| Example 47 | E20 | −1.80 | C21 | −1.05 | 0.75 | 4.0 |

Example 48

In this example, an organic light emitting element of a top emission construction in which a first electrode (anode), a hole transport layer, an electron blocking layer, an emission layer, a hole blocking layer, an electron injection/transport layer, and a second electrode (cathode) were formed in the stated order on a substrate was produced by a method to be described below.

An aluminum metal and indium tin oxide (ITO) were formed into films and laminated in the stated order on a glass substrate (substrate) by a sputtering method. Thus, the first electrode as an anode was formed. At this time, the thickness of the aluminum film constituting the first electrode was set to 100 nm and the thickness of the ITO film constituting the first electrode was set to 30 nm. Next, the substrate having formed thereon the first electrode was sequentially subjected to ultrasonic washing with acetone and isopropyl alcohol (IPA), and was then subjected to boil washing with IPA, followed by drying. Further, the dried product was subjected to UV/ozone washing, to thereby obtain an ITO substrate.

Next, layers and the second electrode as a cathode shown in Table 8 below were continuously formed on the ITO substrate by vacuum deposition based on resistance heating in a vacuum chamber at $10^{-5}$ Pa. At this time, the layers were formed so that an emission area in which the first electrode and the second electrode overlapped each other became 4 mm².

TABLE 8

| | Constituent material | Thickness [nm] |
|---|---|---|
| Hole transport layer | HT2 | 200 |
| Electron blocking layer | HT7 | 10 |
| Emission layer | Host: EM14 Guest: RD1 (Host:guest: = 99.5:0.5 (volume ratio)) | 20 |
| Hole blocking layer | EM15 | 10 |
| Electron injection/transport layer[Note 1] | E19, C3 | 33 |
| Second electrode (cathode)[Note 2] | Aluminum, silver | 30 |

(Note 1)
The electron injection/transport layer is a laminate in which E19 (30 nm, acceptor layer) and C1 (3 nm, donor layer) are laminated in the stated order. In addition, $V_{ox}-V_{red}$ in Example 48 is 0.80 V.
(Note 2)
The second electrode is a laminate in which aluminum (5 nm) and silver (25 nm) are laminated in the stated order.

It should be noted that in the organic light emitting element produced in this example, the second electrode was an optically semitransparent electrode, and was a laminated electrode formed of aluminum (5 nm) and silver (25 nm) in consideration of a reflectance, absorption, and a conductivity. In addition, a cavity construction in which light extraction efficiency was improved by utilizing optical interference was adopted, and the thicknesses of the respective layers were determined so that their interference conditions coincided with each other.

The resultant organic light emitting element was driven so that its luminance became 100 cd/m². As a result, its light emitting efficiency was 3.6 cd/A and red light emission was observed.

(Result and Discussion)

The viologen compound as the electron donor-property compound X is a compound having a shallow LUMO. Accordingly, as is understood from Comparative Example 1, even when an electron injection layer is formed by forming only the viologen compound (electron donor-property compound X) into a film, an electron is not injected from a cathode.

On the other hand, each of the organic light emitting elements of Examples emitted light. The fact shows that in the organic light emitting element of the present invention whose electron injection layer contains the electron donor-property viologen compound X and the electron acceptor-property compound Y, an electron is injected from its cathode by the electron injection layer.

It is understood from the foregoing that the organic light emitting element of the present invention whose electron injection layer has the electron donor-property compound X (viologen compound) and the electron acceptor-property compound Y introduced therein can be stably caused to output light even in the air.

This application claims the benefit of Japanese Patent Application No. 2014-018560, filed Feb. 3, 2014, and Japanese Patent Application No. 2015-001211, filed Jan. 7, 2015, which are hereby incorporated by reference herein in their entirety.

REFERENCE SIGNS LIST 1 display device
11 substrate
15 semiconductor layer
18 TFT element
21 anode
22 organic compound layer
23 cathode
26 image forming device
27 photosensitive member
28 exposure light source
28a elongated substrate
36, 36α, 36β emission portion
37 column direction

The invention claimed is:
1. An organic light emitting element comprising:
an anode;
a cathode; and
an emission layer placed between the anode and the cathode,
wherein the organic light emitting element further comprises:
a first organic compound layer placed between the cathode and the emission layer, and
a second organic compound layer placed between the emission layer and the first organic compound layer, and brought into contact with the first organic compound layer;
wherein the first organic compound layer comprises a first organic compound;
wherein the second organic compound layer comprises a second organic compound;
wherein the first organic compound comprises an organic compound represented by the following general formula [1]; and
wherein the second organic compound comprises an organic compound different from the first organic compound,

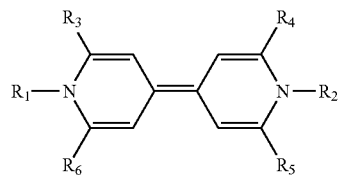

[1]

in the formula [1], $R_1$ to $R_6$ each represent a hydrogen atom or a substituent selected from a fluorine atom, an alkyl group, an alkoxy group, an aryl group and a heteroaryl group; when any one of $R_1$ to $R_6$ represents an alkyl group or an alkoxy group, the alkyl group or the alkoxy group may further have a fluorine atom; and when any one of $R_1$ to $R_6$ represents an aryl group or a heteroaryl group, the aryl group or the heteroaryl group may further have a fluorine atom, an alkyl group, an alkoxy group, or an amino group.

2. The organic light emitting element according to claim 1, wherein the first organic compound layer comprises a layer brought into contact with the cathode.

3. An organic light emitting element comprising:
an anode;
a cathode; and
an emission layer placed between the anode and the cathode,
wherein the organic light emitting element further comprises an organic compound layer placed between the emission layer and the cathode;
wherein the organic compound layer contains a first organic compound and a second organic compound;
wherein the first organic compound comprises an organic compound represented by the following general formula [1]; and
wherein the second organic compound comprises an organic compound different from the first organic compound,

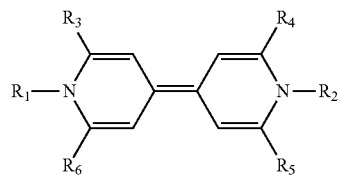

[1]

in the formula [1], $R_1$ to $R_6$ each represent a hydrogen atom or a substituent selected from a fluorine atom, an alkyl group, an alkoxy group, an aryl group and a heteroaryl group; when any one of $R_1$ to $R_6$ represents an alkyl group or an alkoxy group, the alkyl group or the alkoxy group may further have a fluorine atom; and when any one of $R_1$ to $R_6$ represents an aryl group or a heteroaryl group, the aryl group or the heteroaryl group may further have a fluorine atom, an alkyl group, an alkoxy group, or an amino group.

4. The organic light emitting element according to claim 3, wherein the organic compound layer comprises a layer brought into contact with the cathode.

5. The organic light emitting element according to claim 3, wherein a content of the second organic compound is more than 0 wt % and 80 wt % or less with respect to a total of the first organic compound and the second organic compound.

6. The organic light emitting element according to claim 1, wherein the first organic compound and the second organic compound satisfy the following formula [2]:

$$|V_{red} - V_{ox}| \leq 1.0 \text{ V} \quad [2]$$

in the formula [2], $V_{red}$ represents a first reduction potential value of the second organic compound and $V_{ox}$ represents a first oxidation potential value of the first organic compound.

7. The organic light emitting element according to claim 6, wherein the first organic compound and the second organic compound satisfy the following formula [5]:

$$|V_{red} - V_{ox}| \leq 0.5 \text{ V} \quad [5]$$

in the formula [5], $V_{red}$ represents a first reduction potential value of the second organic compound and $V_{ox}$ represents a first oxidation potential value of the first organic compound.

8. The organic light emitting element according to claim 1, wherein the second organic compound comprises a compound represented by any one of the following general formulae [3-1] to [3-21], [4-1], and [4-2]:

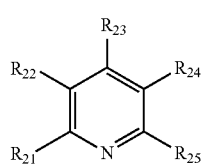
[3-1]

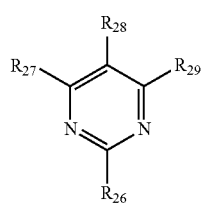
[3-2]

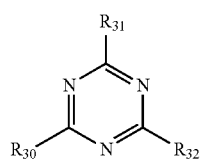
[3-3]

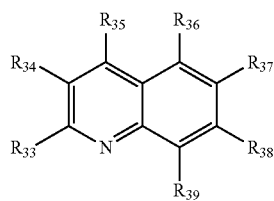
[3-4]

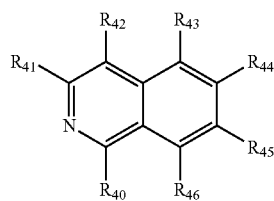
[3-5]

-continued

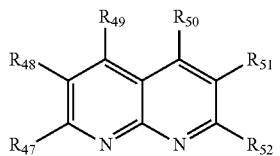
[3-6]

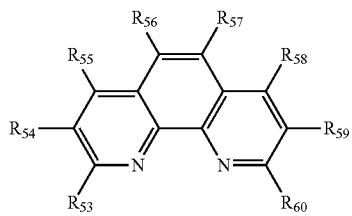
[3-7]

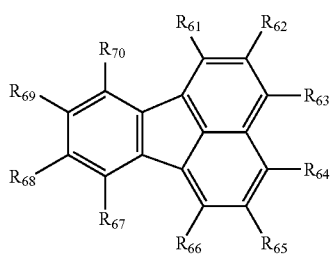
[3-8]

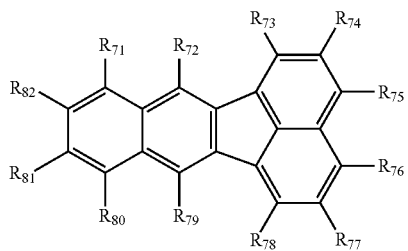
[3-9]

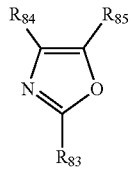
[3-10]

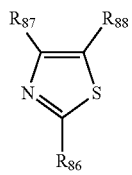
[3-11]

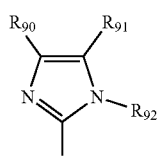
[3-12]

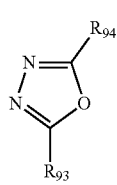
[3-13]

-continued

[3-14]
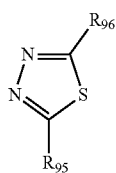

[3-15]
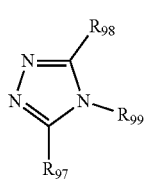

[3-16]
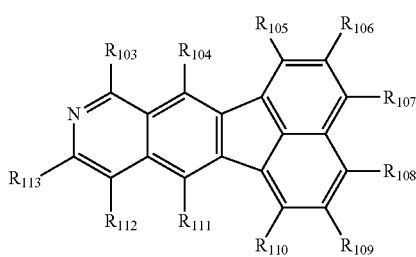

[3-17]
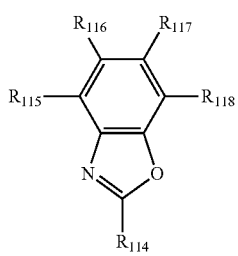

[3-18]
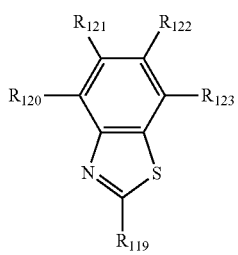

[3-19]
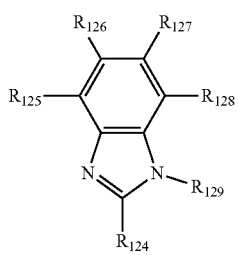

-continued

[3-20]
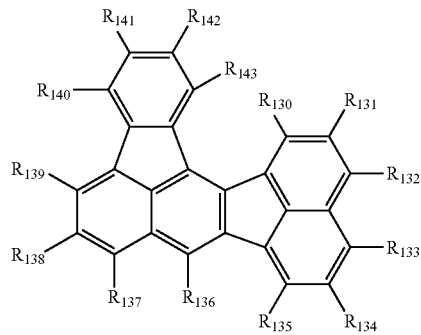

[3-21]
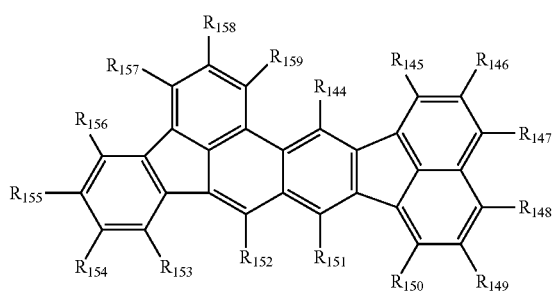

[4-1]
Q—(P)$_n$

[4-2]
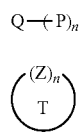

in the formulae [3-1] to [3-21], [4-1], and [4-2], $R_{21}$ to $R_{99}$ and $R_{103}$ to $R_{159}$ each represent a hydrogen atom or a substituent selected from a fluorine atom, an alkyl group, an alkoxy group, an aryl group and a heteroaryl group, and when any one of $R_{21}$ to $R_{99}$ and $R_{103}$ to $R_{159}$ represents an aryl group or a heteroaryl group, the aryl group or the heteroaryl group may further have an alkyl group, an alkoxy group, an aryl group, a heteroaryl group, or a fluorine atom;

in the formula [4-1], a unit Q represents a basic structure represented by any one of the formulae [3-1] to [3-21] or a partial structure including an aromatic ring having 6 to 30 carbon atoms, m represents an integer of from 0 to 6, and a unit P represents any one of the following substituents:

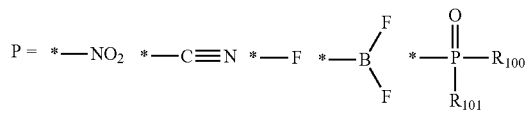

in the formulae, $R_{100}$ and $R_{101}$ each represent a hydrogen atom or a substituent selected from an alkyl group, an alkoxy group, an aryl group, a heteroaryl group and a fluorine atom, and when any one of $R_{100}$ and $R_{101}$ represents an aryl group or a heteroaryl group, the aryl group or the heteroaryl group may further have an alkyl group, an alkoxy group, an aryl group, a heteroaryl group, or a fluorine atom, and * represents a bonding hand with the unit Q; and in the formula [4-2], a unit T represents a partial structure including an aromatic ring having 6 to 30 carbon atoms or a partial structure including a five- or six-membered heterocyclic structure formed of a carbon atom and an oxygen atom, n represents an integer of from 0 to 6, and a unit Z represents any one of the following substituents:

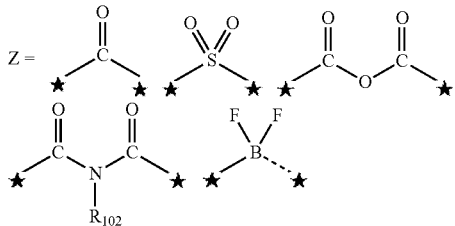

in the formulae, $R_{102}$ represents a substituent selected from a hydrogen atom, an alkyl group, an alkoxy group, an aryl group, a heteroaryl group and a fluorine atom, and when $R_{102}$ represents an aryl group or a heteroaryl group, the aryl group or the heteroaryl group may further have an alkyl group, an alkoxy group, an aryl group, a heteroaryl group, or a fluorine atom, and ★ represents a bonding hand with the unit T.

9. The organic light emitting element according to claim 1, wherein the first organic compound comprises an organic compound represented by the following general formula [6]:

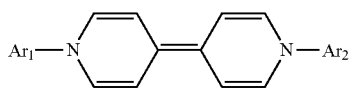

[6]

in the general formula [6], $Ar_1$ and $Ar_2$ each represent an aryl group that may have a fluorine atom, an alkyl group, an alkoxy group, or an amino group.

10. The organic light emitting element according to claim 1, wherein the first organic compound comprises an organic compound represented by the following general formula [8]:

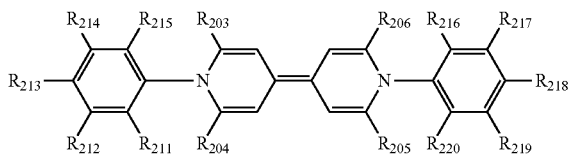

[8]

in the general formula [8], all of $R_{203}$ to $R_{206}$ represent aryl groups, and $R_{211}$ to $R_{220}$ each represent a hydrogen atom or a substituent selected from a fluorine atom, an alkyl group, an alkoxy group, and an aryl group, provided that the aryl group may further have a fluorine atom, an alkyl group, an alkoxy group, or an amino group.

11. A display device comprising a plurality of pixels, wherein at least one of the plurality of pixels includes the organic light emitting element of claim 1 and an active element connected to the organic light emitting element.

12. The display device according to claim 11, wherein the active element comprises a transistor and the transistor has an oxide semiconductor as an active layer.

13. An image information processing device comprising:
an input portion configured to input image information; and
a display portion configured to display an image,
wherein the display portion comprises the display device of claim 11.

14. A lighting device comprising:
the organic light emitting element of claim 1; and
an AC/DC converter configured to supply a driving voltage to the organic light emitting element.

15. An image forming device comprising:
a photosensitive member;
a charging portion configured to charge the photosensitive member;
an exposure portion configured to expose the photosensitive member; and
a developing portion configured to apply a developer to the photosensitive member,
wherein the exposure portion includes the organic light emitting element of claim 1.

16. An exposing device, which is configured to expose a photosensitive member, the exposing device comprising a plurality of emission points each including the organic light emitting element of claim 1, wherein the plurality of emission points are placed to form a line along a long axis direction of the photosensitive member.

* * * * *